(12) United States Patent
Watanabe

(10) Patent No.: US 9,487,443 B2
(45) Date of Patent: Nov. 8, 2016

(54) LAYER STACK FORMATION POWDER MATERIAL, POWDER LAYER STACK FORMATION HARDENING LIQUID, LAYER STACK FORMATION MATERIAL SET, AND LAYER STACK OBJECT FORMATION METHOD

(71) Applicant: Masaki Watanabe, Shizuoka (JP)

(72) Inventor: Masaki Watanabe, Shizuoka (JP)

(73) Assignee: RICOH COMPANY, LTD., Tokyo (JP)

( * ) Notice: Subject to any disclaimer, the term of this patent is extended or adjusted under 35 U.S.C. 154(b) by 69 days.

(21) Appl. No.: 14/621,720

(22) Filed: Feb. 13, 2015

(65) Prior Publication Data

US 2015/0259247 A1    Sep. 17, 2015

(30) Foreign Application Priority Data

| Mar. 14, 2014 | (JP) | 2014-052111 |
| Mar. 14, 2014 | (JP) | 2014-052119 |
| Mar. 14, 2014 | (JP) | 2014-052129 |
| Oct. 3, 2014 | (JP) | 2014-204782 |
| Oct. 3, 2014 | (JP) | 2014-204804 |

(51) Int. Cl.

| B28B 1/00 | (2006.01) |
| A61F 2/28 | (2006.01) |
| A61L 27/12 | (2006.01) |
| C04B 12/02 | (2006.01) |
| B33Y 70/00 | (2015.01) |
| B28B 7/46 | (2006.01) |
| A61F 2/30 | (2006.01) |

(52) U.S. Cl.
CPC ............... *C04B 12/025* (2013.01); *A61F 2/28* (2013.01); *A61L 27/12* (2013.01); *B28B 1/001* (2013.01); *B28B 7/465* (2013.01); *B33Y 70/00* (2014.12); *A61F 2002/30985* (2013.01); *A61L 2430/02* (2013.01)

(58) Field of Classification Search
None
See application file for complete search history.

(56) References Cited

U.S. PATENT DOCUMENTS

| 5,204,055 A | 4/1993 | Sachs et al. |
| 5,902,441 A | 5/1999 | Bredt et al. |
| 6,322,728 B1 | 11/2001 | Brodkin et al. |
| 6,375,874 B1 | 4/2002 | Russell et al. |

(Continued)

FOREIGN PATENT DOCUMENTS

| JP | 04-321507 | 11/1992 |
| JP | 05-237278 | 9/1993 |

(Continued)

*Primary Examiner* — Mary F Theisen
(74) *Attorney, Agent, or Firm* — Cooper & Dunham LLP

(57) ABSTRACT

Layer stack object formation method, including; forming layer of powder material containing calcium phosphate; and delivering hardening liquid to predetermined region of the layer to harden the region, wherein these steps are repeated, wherein 1) powder material satisfies A) or B), and hardened product of powder material has hydroxyapatite (HAp) transformation rate of ≤1%: A) organic compound having phosphate or carboxyl group is imparted over surface of calcium phosphate powder, and organic compound imparting amount is ≤10,000 ppm; and B) powder material further contains powder made of organic compound having phosphate or carboxyl group, and organic compound mixing amount to calcium phosphate powder is ≤50% by mass, or wherein 2) hardening liquid contains at least organic compound having phosphate or carboxyl group, acid value of organic compound is ≥0.45 gKOH/g, and content of organic compound to whole amount of hardening liquid is ≥20% by mass.

19 Claims, 2 Drawing Sheets

(56) References Cited

U.S. PATENT DOCUMENTS

| | | |
|---|---|---|
| 2002/0064745 A1 | 5/2002 | Schulman et al. |
| 2003/0030170 A1* | 2/2003 | Abe .................. B29C 67/0081 264/113 |
| 2005/0046067 A1* | 3/2005 | Oriakhi ................ B28B 1/00 264/113 |
| 2005/0087903 A1* | 4/2005 | Farr .................. B28B 1/001 264/113 |
| 2007/0009606 A1* | 1/2007 | Serdy .................. A61F 2/28 424/497 |
| 2007/0181239 A1 | 8/2007 | Yamazawa et al. |
| 2015/0374497 A1* | 12/2015 | Engstrand .............. A61F 2/2846 623/17.19 |

FOREIGN PATENT DOCUMENTS

| | | |
|---|---|---|
| JP | 08-090648 | 4/1996 |
| JP | 09-324203 | 12/1997 |
| JP | 2004-042546 | 2/2004 |
| JP | 2004-202126 | 7/2004 |
| JP | 3712203 | 8/2005 |
| JP | 3965249 | 6/2007 |
| JP | 4575295 | 8/2010 |
| JP | 2012-228383 | 11/2012 |

* cited by examiner

LAYER STACK FORMATION POWDER MATERIAL, POWDER LAYER STACK FORMATION HARDENING LIQUID, LAYER STACK FORMATION MATERIAL SET, AND LAYER STACK OBJECT FORMATION METHOD

BACKGROUND OF THE INVENTION

1. Field of the Invention

The present invention relates to a layer stack formation powder material, a powder layer stack formation hardening liquid, a layer stack formation material set, and a layer stack object formation method.

2. Description of the Related Art

Conventionally, artificial bones have been produced from metallic materials such as stainless and a titanium alloy, wear-resistant plastics, etc., and used for bone replacement. Such artificial bones act in place of dysfunctional joints, but problematically cannot endure a long time of use, because metallic materials and wear-resistant plastics incur aging changes such as wear, corrosion, and swell. Ceramics based on calcium phosphate can be raised as a material to replace them. Currently known ceramics include those for providing scaffolding for bone formation, and those that promote formation of new bones while themselves being absorbed into the bones along with time, and transform to bones in the future.

As bone prosthetic materials for providing scaffolding for bone formation, for example, materials such as hydroxyapatite that have excellent affinity with bone tissues and directly attach to bone tissues without a mediating material are often used. With implantation of such a bone prosthetic material into a bone defect portion, bone repair advances swiftly based on the scaffolding of the bone prosthetic material. However, hydroxyapatite cannot transform to bones by itself, and there is a risk that residual hydroxyapatite may cause troubles in the living bodies. On the other hand, any bone prosthetic material that can transform to bones can, when implanted in bone tissues, promote the osteogenic action of the bone tissues and advance bone repair easily and more swiftly.

For example, tricalcium phosphate is known as such a material that can transform to bones. The degree of how tricalcium phosphate is absorbed into bone tissues is dependent on the shape and texture of an object made of tricalcium phosphate. That is, a porous texture object has a large surface area due to its texture, can be absorbed into bone tissues easily, and also can be phagocytosed by phagocytic cells easily. In contrast, a dense texture object is absorbed extremely slowly, and cannot be phagocytosed by phagocytic cells easily. It is expected that utilizing the characteristic differences due to the texture, and combining a porous texture portion and a dense texture portion would lead to expression of a desired biocompatibility (see Japanese Patent Application Laid-Open (JP-A) No. 05-237278). However, none of such combination materials have strength of a level applicable as a thighbone that receives a heavy load. Further, not only does it take a long time to form such materials into a desired shape, but it is impossible to make them into a fine shape including an internal structure, particularly in the case where this process is by cutting.

Techniques of forming real three-dimensional objects based on three-dimensional shape data generated by 3D CAD or the like are generically called rapid prototyping techniques. According to an object formation method using a highly heat-resistant powder as a material among such rapid prototyping techniques, it is possible to produce a mold or a core cylinder without using a model or a wooden pattern, which makes it possible to realize an extremely fast foundry production process.

This rapid prototyping technique is also called layer stack formation method, and stacks up cross-sectional shapes of an object as layers, and forms a three-dimensional object. Furthermore, there are proposed various layer stacking methods that are one type of the rapid prototyping techniques, and use a powder as a material (powder adherence methods) (see, e.g., U.S. Pat. Nos. 5,204,055, 5,902,441, 6,375,874, JP-A No. 09-324203, and JP-A No. 2004-42546).

For example, there is proposed a technique for "an artificial bone forming method by powder lamination method", wherein the technique forms a powder bone material that hardens by hydration into a powder layer, to thereby form an artificial bone having a greater strength (see Japanese Patent (JP-B) No. 4575295). However, it is difficult to obtain a sufficient strength based on hardening by hydration proposed, and in particular, it is difficult to apply such a material at a portion that receives a load, such as a thighbone.

This powder lamination object formation method is advantageous for fine shaping mentioned above. However, calcium phosphate reactive with water as used in JP-B No. 4575295 tends to transform to unabsorbable hydroxyapatite by being transplanted into a living body. In this case, the transplanted material may remain in the body for a long term and cause troubles as described above.

Hence, it is preferable that the transplanted material be not left transformed to a crystal in the body, but be left there in a state of having potential to transform to a bone eventually. Further, for powder layer stack formation by ink jetting, it is preferable that the powder harden as soon as possible after a hardening liquid lands on the powder. Hence, it is requested to provide a hardening liquid for powder layer stack formation that can impart a bone transformation ability to the powder, can harden the powder quickly, and can form a layer stack object having a complex three-dimensional shape with a high strength and a good precision.

Calcium phosphate transplanted into a living body may not transform to a bone at a satisfactory speed, or an artificial bone implanted by a medical operation may require a considerable time before it is high time to remove an external fixator. When bone regeneration is slow, it is feared that a soft tissue may wander into the bone defect portion and inhibit bone regeneration. To promote bone regeneration, it is proposed to add a bonemaking protein such as BMP. However, even when an object made of calcium phosphate containing a bonemaking protein is formed by ink jetting, the protein will be deactivated and become ineffective if the object is burned afterwards. Hence, for object formation by ink jetting, it is preferable that a bonemaking protein be added after burning, or that bone regeneration be realized with an inorganic material that will not become ineffective even when burned. Examples of such an inorganic material include minerals such as silicon and zinc.

SUMMARY OF THE INVENTION

An object of the present invention is to provide a layer stack object formation method that can form with a high strength and a good precision, a layer stack object that scarcely transforms to unabsorbable hydroxyapatite when transplanted into a living body, and has a high hardening speed, a high bone inducing ability, and a complex three-dimensional shape.

As a solution to the problems described above, a layer stack object formation method of the present invention includes:

a layer forming step of forming a layer of a powder material containing calcium phosphate; and a layer hardening step of delivering a hardening liquid to a predetermined region of the layer to thereby harden the region, wherein the layer forming step and the layer hardening step are repeated, and wherein 1) or 2) described below is satisfied, 1) the powder material satisfies A) or B) described below, and a hardened product obtained by hardening the powder material has a hydroxyapatite (HAp) transformation rate of 1% or lower, A) an organic compound having phosphate group or carboxyl group is imparted over a surface of a powder of the calcium phosphate, and an imparting amount of the organic compound is 10,000 ppm or lower, and B) the powder material further contains a powder made of an organic compound having phosphate group or carboxyl group, and a mixing amount of the organic compound relative to a powder of the calcium phosphate is 50% by mass or lower, and 2) the hardening liquid contains at least an organic compound having phosphate group or carboxyl group, an acid value of the organic compound is 0.45 gKOH/g or higher, and a content of the organic compound relative to a whole amount of the hardening liquid is 20% by mass or higher.

The present invention can solve the conventional problems described above, achieve the object described above, and provide a layer stack object formation method that can form with a high strength and a good precision, a layer stack object that scarcely transforms to unabsorbable hydroxyapatite when transplanted into a living body, and has a high hardening speed, a high bone inducing ability, and a complex is three-dimensional shape.

DETAILED DESCRIPTION OF THE INVENTION

Powder Layer Stack Formation Hardening Liquid

Figure 1:
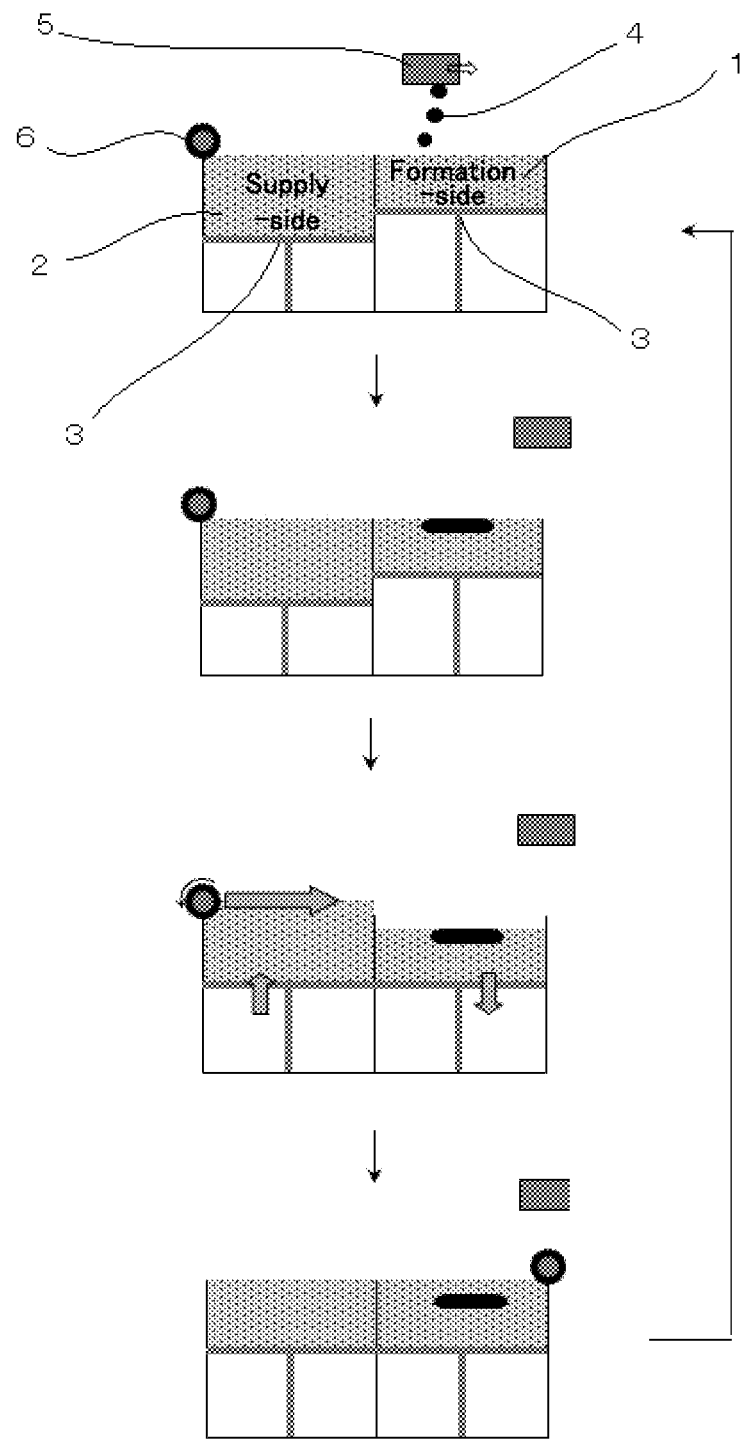
FIG. 1 is a schematic diagram showing an example of a powder layer stack formation apparatus used in the present invention.

A powder layer stack formation hardening liquid of the present invention contains an organic compound having phosphate group or carboxyl group, preferably contains inorganic particles, an aqueous medium, a viscosity modifier, a surfactant, and an antifoaming agent, and further contains other components according to necessity.

In the present invention, it is preferable that the powder layer stack formation hardening liquid be water-soluble. Being water-soluble means that the materials constituting the powder layer stack formation hardening liquid can dissolve in water in an amount of 30% by mass or higher.

<Organic Compound Having Phosphate Group>

It is preferable that the organic compound having phosphate group be a chelate material that has an ability to capture a calcium ion contained in calcium phosphate, is non-toxic to a human body, and can be egested easily.

Examples of the organic compound having phosphate group include alendronic acid, etidronic acid, and phytic acid. Among these, etidronic acid and phytic acid that have 2 or more phosphate groups per molecule are more preferable because more phosphate groups per molecule is preferable in order to improve the calcium ion capture ability.

The acid value of the organic compound having phosphate group is 0.45 gKOH/g or higher, and more preferably from 0.45 gKOH/g to 1.00 gKOH/g. When the acid value is 0.45 gKOH/g or higher, advantages such as a high hardening speed, and an improved strength of a structure obtained by layer stack formation can be achieved.

The acid value can be measured according to, for example, a method described in JIS K0070-1992.

The organic compound having phosphate group is suitable for use with $\beta$-tricalcium phosphate ($\beta$-TCP), $\alpha$-tricalcium phosphate ($\alpha$-TCP), tetracalcium phosphate, octacalcium phosphate (OCP), etc. that undergo bone transformation. Among these, materials such as $\alpha$-tricalcium phosphate and octacalcium phosphate that have a risk of transforming to hydroxyapatite by reacting with water, and particularly, $\alpha$-tricalcium phosphate, are/is the material(s) with which the organic compound having phosphate group is suitable for use. In this case, if the organic compound having phosphate group has a low calcium ion capture ability, these materials may transform to unabsorbable hydroxyapatite when transplanted into a living body, and may lose the bone transformation ability.

The content of the organic compound having phosphate group is 20% by mass or higher, and preferably 30% by mass or higher relative to the whole amount of the powder layer stack formation hardening liquid. When the content is 20% by mass or higher, the hardening speed will be adequate, and a structure to be obtained by layer stack formation will have a favorable strength.

<Organic Compound having Carboxyl Group>

It is preferable that the organic compound having carboxyl group be a chelate material that has an ability to capture a calcium ion contained in calcium phosphate, is non-toxic to a human body, and can be egested easily.

Examples of the organic compound having carboxyl group include malic acid, succinic acid, citric acid, and edetic acid. Among these, citric acid that has 3 or more carboxyl groups per molecule and is water-soluble is more preferable because more carboxyl groups per molecule is preferable in order to improve the calcium ion capture ability.

The acid value of the organic compound having carboxyl group is 0.45 gKOH/g or higher, and more preferably from 0.45 gKOH/g to 1.00 gKOH/g. When the acid value is 0.45 gKOH/g or higher, advantages such as a high hardening speed, and an improved strength of a structure to be obtained by layer stack formation can be achieved.

The acid value can be measured according to, for example, a method described in JIS K0070-1992.

The organic compound having carboxyl group is suitable for use with $\beta$-tricalcium phosphate ($\beta$-TCP), $\alpha$-tricalcium phosphate ($\alpha$-TCP), tetracalcium phosphate, octacalcium phosphate (OCP), etc. that undergo bone transformation. Among these, materials such as $\alpha$-tricalcium phosphate and octacalcium phosphate that have a risk of transforming to hydroxyapatite by reacting with water, and particularly, $\alpha$-tricalcium phosphate, are/is the material(s) with which the organic compound having carboxyl group is suitable for use. In this case, if the organic compound having carboxyl group has a low calcium ion capture ability, these materials may transform to unabsorbable hydroxyapatite when transplanted into a living body, and may lose the bone transformation ability.

The content of the organic compound having carboxyl group is 20% by mass or higher, and preferably 30% by mass or higher relative to the whole amount of the powder layer stack formation hardening liquid. When the content is 20% by mass or higher, the hardening speed will be adequate, and a structure to be obtained by layer stack formation will have a favorable strength.

<Inorganic Particles>

When added in the powder layer stack formation hardening liquid, the inorganic particles can impart an effect of promoting bone regeneration.

The inorganic particles are not particularly limited, and arbitrary inorganic particles may be selected according to the purpose. Examples thereof include silica and zinc. Of these, silica is preferable.

The inorganic particles may be added as is in the form of inorganic particles in the powder layer stack formation hardening liquid. However, when silica particles are used as the inorganic particles, it is preferable that silica particles be added in the form of an antifoaming agent containing silica particles.

The volume average particle diameter of the inorganic particles is preferably 10 μm or less, and more preferably from 1 μm to 10 μm. When the volume average particle diameter is 10 μm or less, the inorganic particles would not cause a discharge failure when the powder layer stack formation hardening liquid is discharged, because the inorganic particles would not clog the nozzles of a head of an inkjet printer that have a typical nozzle diameter of from 20 μm to 30 μm.

The volume average particle diameter of the inorganic particles can be measured, for example, at 23° C. at 55% RH with MICROTRACK UPA manufactured by Nikkiso Co., Ltd. according to a dynamic light scattering method.

The content of the inorganic particles is not particularly limited, and may be appropriately selected according to the purpose. However, it is preferably from 0.1% by mass to 1.0% by mass relative to the whole amount of the powder layer stack formation hardening liquid.

<Aqueous Medium>

Examples of the aqueous medium include: water; alcohol such as ethanol; ether; and ketone. Among these, water is preferable. The water as the aqueous medium may contain a slight amount of any other component than water, such as alcohol.

The content of the aqueous medium is not particularly limited, and may be appropriately selected according to the purpose.

<Surfactant>

The surfactant is not particularly limited, and an arbitrary surfactant may be selected according to the purpose. Examples thereof include: a negative ion surfactant (anionic surfactant) such as alkyl benzene sulfonic acid salt, α-olefin sulfonic acid salt, phosphoric acid ester, phosphoric acid ester, disulfonic acid salt, cholic acid salt, and deoxycholic acid salt; a positive ion surfactant (cationic surfactant) such as an amine salt type (e.g., alkyl amine salt, amino alcohol fatty acid derivative, polyamine fatty acid derivative, and imidazoline), and a quaternary ammonium salt type (e.g., alkyl trimethyl ammonium salt, dialkyl dimethyl ammonium salt, alkyl dimethyl benzyl ammonium salt, pyridinium salt, alkyl isoquinolinium salt, and benzethonium chloride); a nonionic surfactant such as fatty acid amide derivative, multivalent alcohol derivative, poly(oxyethylene)=octyl phenyl ether; and an amphoteric surfactant such as alanine, dodecyldi(aminoethyl)glycine, di(octylaminoethyl)glycine, N-alkyl-N,N-dimethyl ammonium betaine, and 3-[(3-cholamidopropyl)dimethylammonio]propanesulfonate (CHAPS). One of these may be used alone, or two or more of these may be used in combination. Among these, a surfactant that is liquid at room temperature (20° C.) is preferable in order to suppress clogging of nozzles of an inkjet head.

The content of the surfactant is preferably 1% by mass or less, and more preferably from 0.1% by mass to 0.5% by mass relative to the whole amount of the powder layer stack formation hardening liquid. When the content is 1% by mass or less, the surfactant does not express cytotoxicity when a layer stack object is transplanted into a living body, because the residual amount of the surfactant in the layer stack object is low. Further, any residue of the surfactant that is left even after the layer stack object is burned does not cause troubles in a living body and is safe.

<Antifoaming Agent>

Examples of the antifoaming agent include a silicone antifoaming agent containing silica particles, such as a compound-type silicone antifoaming agent, an emulsion-type silicone antifoaming agent, and a self-emulsifying-type silicone antifoaming agent.

The compound-type silicone antifoaming agent is an oil-type silicone antifoaming agent in which particles of silica, alumina, or the like are dispersed in order to have a better antifoaming property.

The emulsion-type silicone antifoaming agent is a compound-type antifoaming agent formed into an O/W-type emulsion by an emulsifier in order to have a better water dispersibility.

The self-emulsifying-type silicone antifoaming agent contains a silicone oil and silica, and changes to an O/W-type emulsion easily when diluted with water.

When a surfactant is used in the powder layer stack formation hardening liquid of the present invention, the powder layer stack formation hardening liquid has a poor surface tension and bubbles up easily. Hence, among the silicone antifoaming agents described above, a compound-type silicone antifoaming agent, an emulsion-type silicone antifoaming agent, and a self-emulsifying-type silicone antifoaming agent that contain silica having an excellent antifoaming property are preferable.

The silicone antifoaming agent may be a commercially available product. Examples of commercially available products include: KS-508, KS-531, KM-72, KM-72F, KM-73, KM-90, and KM-98 (all manufactured by Shin-Etsu Chemical Co., Ltd.); SF-8427, SF-8428, SH-3749, SH-8400, FZ-2101, FZ-2104, FZ-2118, FZ-2203, and FZ-2207 (all manufactured by Dow Corning Toray Co., Ltd.); and BYK-345, BYK-346, and BYK-348 (all manufactured by Byk-Chemie Japan K.K.). One of these may be used alone, or two or more of these may be used in combination.

A typical purpose of adding the antifoaming agent, in the case of adding it in a powder layer stack formation hardening liquid, is to improve various properties of the hardening liquid, such as discharge stability and storage stability. Silica particles contained in the antifoaming agent, which are inorganic particles, are known to have an effect of promoting bone regeneration. Therefore, this fact is preferable because a state of silica particles being contained in a layer stack object in a predetermined amount can be created in a powder layer stack formation process.

The content of the antifoaming agent is preferably from 0.005% by mass to 3% by mass, and more preferably from 0.01% by mass to 0.5% by mass relative to the whole amount of the powder layer stack formation hardening liquid. When the content is 0.005% by mass or greater, an antifoaming property can be improved sufficiently, which improves a bone regeneration inducing ability and brings about sufficient bone transformation. When the content is 3% by mass or less, a bone regeneration inducing ability is improved, and the powder layer stack formation hardening liquid can have favorable storage stability and discharge stability.

<Viscosity Modifier>

In order to adjust the viscosity of the powder layer stack formation hardening liquid, it is preferable that the hardening liquid contain a viscosity modifier according to necessity. Note that the organic compound having phosphate group or carboxyl group also serves as a viscosity modifier.

The viscosity modifier is not particularly limited, and an arbitrary viscosity modifier may be selected according to the purpose. Examples thereof include multivalent alcohol such as glycerin, the organic compound having phosphate group or carboxyl group, a water-soluble polysaccharide, a water-soluble resin, and a water-soluble prepolymer.

The content of the viscosity modifier is not particularly limited, and may be appropriately selected depending on the kind of the viscosity modifier. For example, when glycerin is used as the viscosity modifier, the content is preferably from 20% by mass to 40% by mass.

<Other Components>

Publicly-known other components that may be added in the powder layer stack formation hardening liquid are not particularly limited, and arbitrary components may be selected according to the purpose. Examples thereof include a preserving agent, an antiseptic, a stabilizing agent, and a pH adjustor.

—Physical Properties, Etc. of Powder Layer Stack Formation Hardening Liquid—

The viscosity of the powder layer stack formation hardening liquid is preferably from 5 mPa·s to 20 mPa·s, and more preferably from 8 mPa·s to 15 mPa·s at 20° C. When the viscosity is 5 mPa·s or higher or 20 mPa·s or lower, the hardening liquid will be discharged stably from the inkjet nozzles, and a hardened object formed by delivering the powder layer stack formation hardening liquid to layers of a layer stack formation powder material will have a sufficient strength, will not cause troubles such as a shape collapse during a post-treatment or handling such as sintering, and will have a good dimensional precision.

The viscosity can be measured according to, for example, JIS K7117.

The surface tension of the powder layer stack formation hardening liquid is preferably 40 N/m or lower, or more preferably from 1 N/m to 30 N/m at 20° C. When the surface tension is 40 N/m or lower, the hardening liquid will be discharged stably from the inkjet nozzles, and a hardened object formed by delivering the powder layer stack formation hardening liquid to layers of a layer stack formation powder material will have a sufficient strength, will not cause troubles such as a shape collapse during a post-treatment or handling such as sintering, and will have a good dimensional precision.

The surface tension can be measured, for example, with DY-300 manufactured by Kyowa Interface Science Co., Ltd.

The powder layer stack formation hardening liquid can be used suitably for simplified efficient formation of various objects or structures, and can be used particularly suitably with the layer stack formation material set of the present invention, and the layer stack object formation method and layer stack object formation apparatus of the present invention, which are described below.

(Layer Stack Formation Powder Material)

A layer stack formation powder material of the present invention contains a calcium phosphate powder, and has an organic compound having phosphate group or carboxyl group exist over the surface of the calcium phosphate powder, or alternatively contains a calcium phosphate powder and a powder with the latter powder being an organic compound having phosphate group or carboxyl group, and further contains other components according to necessity.

<Calcium Phosphate Powder>

The calcium phosphate powder is not particularly limited except that it should have a form of a powder or particles, and an arbitrary calcium phosphate powder may be selected according to the purpose. Examples of the material thereof include hydroxyapatite, carbonate apatite, fluorinated apatite, β-tricalcium phosphate (β-TCP), α-tricalcium phosphate (α-TCP), tetracalcium phosphate, and octacalcium phosphate (OCP). One of these may be used alone, or two or more of these may be used in combination.

Among these, β-tricalcium phosphate (β-TCP), α-tricalcium phosphate (α-TCP), and octacalcium phosphate (OCP) are preferable in order to obtain a layer stack object that will transform to a bone.

Commercially available particles or powders made of these materials may be used as the calcium phosphate. Examples of commercially available products include β-TCP (manufactured by Taihei Chemical Industrial Co., Ltd.), and α-TCP (manufactured by Taihei Chemical Industrial Co, Ltd.). A publicly-known surface (reforming) treatment may be applied to the calcium phosphate, for such purposes as improving aggregability thereof.

A method for producing the calcium phosphate powder is not particularly limited, and an arbitrary method may be selected according to the purpose. Examples thereof include a precipitation method that is used favorably for synthesizing hydroxyapatite (HAp).

<Imparting of Organic Compound Having Phosphate Group or Carboxyl Group>

An organic compound having phosphate group or carboxyl group is imparted onto the surface of the calcium phosphate powder. Hence, even when calcium phosphate reactive with water is transplanted into a living body, it will scarcely transform to unabsorbable hydroxyapatite owing to the functioning of the imparted organic compound, which means that a layer stack formation powder material with which it is possible to form a layer stack object having no cytotoxicity and having a complex three-dimensional shape easily, efficiently, with a high strength, and with a good dimensional precision can be obtained.

For imparting, it is only necessary that the organic compound be existent over the surface of the calcium phosphate powder, and modes of existence include adsorption, coating, carrying, inclusion, etc.

It is preferable that the organic compound be a chelate material that has an ability to capture a calcium ion contained in calcium phosphate, is non-toxic to a human body, and can be egested easily.

The organic compound having phosphate group is suitable for use with β-tricalcium phosphate (β-TCP), α-tricalcium phosphate (α-TCP), tetracalcium phosphate, octacalcium phosphate (OCP), etc. that undergo bone transformation. Among these, materials such as α-tricalcium phosphate and octacalcium phosphate that have a risk of transforming to hydroxyapatite by reacting with water are the materials with which the organic compound having phosphate group is suitable for use. In this case, if the organic compound has a low calcium ion capture ability, these materials may transform to unabsorbable hydroxyapatite when let into a living body, and may lose the bone transformation ability.

It is preferable that the organic compound having phosphate group be one that has 2 or more phosphate groups per molecules, and examples thereof include alendronic acid, etidronic acid, and phytic acid. Among these, phytic acid is more preferable in order to improve the calcium ion capture ability, because phytic acid has many phosphate groups per molecule are more preferable because more phosphate groups per molecule.

It is preferable that the organic compound having carboxyl group be one that has 2 or more carboxyl groups per molecule, and examples thereof include citric acid.

The imparting amount of the organic compound to the calcium phosphate powder is 10,000 ppm or less, preferably from 1,000 ppm to 10,000 ppm, more preferably 3,000 ppm to 10,000 ppm, and yet more preferably from 3,000 ppm to 8,000 ppm. When the imparting amount is 1,000 ppm or greater, it is possible to prevent any calcium ion from being left without being formed into a chelate by the organic compound when transplanted into a living body, lest such a calcium ion become a nucleus of transforming to hydroxyapatite. On the other hand, when the imparting amount is 10,000 ppm or less, safety is ensured because no cytotoxicity is expressed upon transplantation into a living body.

The imparting amount (abundance) of the organic compound having phosphate group can be measured with a publicly-known elemental analyzer, e.g., ICPE-9000 (manufactured by Shimadzu Corporation) according to a publicly-known method.

The imparting amount (abundance) of the organic compound having carboxyl group can be measured by, for example, NMR, GC-MS, and LC-MS.

A method for imparting the organic compound to the calcium phosphate powder is not particularly limited, and an arbitrary method may be selected according to the purpose. Preferable examples thereof include a tumbling fluidized bed coating method, a spray drying method, a stirring mixing addition method, a dipping method, and a kneader coating method. These imparting methods can be practiced with various publicly-known coating machines and granulating machines.

<Mixing of Powder Made of Organic Compound Having Phosphate Group or Carboxyl Group>

A mixture of the calcium phosphate powder with a powder made of an organic compound having phosphate group or carboxyl group may be used as the layer stack formation powder material. In this case, upon being landed on by water or a hardening liquid, i.e., hardening agent-containing water that is discharged from an inkjet head, this layer stack formation powder material lets the phosphate group or the carboxyl group constituting the layer stack formation powder material be dissolved in water and react with a calcium ion contained in the calcium phosphate powder, which enables the calcium ion contained in the calcium phosphate powder to be chelated. When such terminally-blocked calcium phosphate is transplanted into a living body, it will scarcely transform to unabsorbable hydroxyapatite owing to the functioning of the imparted phosphate group or carboxyl group, which means that a layer stack formation powder material with which it is possible to form a layer stack object having no cytotoxicity and having a complex three-dimensional shape easily, efficiently, with a high strength, and with a good dimensional precision can be obtained.

The powder made of an organic compound having phosphate group or carboxyl group may be the organic compound having phosphate group or carboxyl group described above, is preferably a chelate material that has an ability to capture a calcium ion contained in the calcium phosphate powder, is non-toxic to a human body, and can be egested easily, and is particularly preferably phytic acid, etidronic acid, or citric acid.

It is preferable that the powder made of an organic compound having phosphate group or carboxyl group be a water-soluble powder, and that it be not a salt because it will not express a sufficient chelating ability when it is in a state of a salt such as a sodium salt.

Here, what is meant by the "water-soluble powder" being "water-soluble" is that the solute can dissolve in water in an amount of 50% by mass or higher at normal temperature.

Further, because phytic acid and etidronic acid are liquid at normal temperature, it is preferable to use powder products of these acids obtained by freeze drying, spray drying, or the like.

The mixing amount of the powder made of an organic compound having phosphate group or carboxyl group relative to the calcium phosphate powder is 50% by mass or less, preferably from 10% by mass to 50% by mass, and more preferably from 10% by mass to 30% by mass. When the mixing amount is 10% by mass or greater, there is no risk of leaving any calcium ion not formed into a chelate by the organic compound when transplanted into a living body, lest such a calcium ion become a nucleus of transforming to hydroxyapatite. On the other hand, when the mixing amount is 50% by mass or less, safety is ensured because no cytotoxicity is expressed upon transplantation into a living body.

A method for mixing the powder made of an organic compound having phosphate group or carboxyl group with the calcium phosphate powder is not particularly limited, and an arbitrary method may be selected according to the purpose. Preferable examples thereof include a stirring mixing addition method.

<Other Components>

Publicly-known other components that may be added in the layer stack formation powder material are not particularly limited, and arbitrary components may be selected according to the purpose. Examples include a fluidizer, a filler, a leveling agent, and a sintering aid.

Addition of the fluidizer in the layer stack formation powder material is preferable because this makes it possible to form a layer or the like of the layer stack formation powder material easily and efficiently. Addition of the filler is preferable because this makes it difficult for voids or the like to be produced in a hardened object to be obtained (layer stack object or hardened object for sintering). Addition of the leveling agent is preferable because this improves wettability of the layer stack formation powder material and makes it easy to handle the powder material. Addition of the sintering aid is preferable because this makes it possible for a hardened object obtained (layer stack object or hardened object for sintering) to be sintered at a lower temperature, when performing sintering.

—Physical Properties, Etc. of Layer Stack Formation Powder Material—

The volume average particle diameter Dv of the layer stack formation powder material is preferably from 1.5 µm to 10.0 µm, more preferably from 1.5 µm to 7.0 µm, yet more preferably from 3.0 µm to 7.0 µm, and particularly preferably from 2.0 µm to 5.0 µm. When the volume average particle diameter Dv is 1.5 µm or greater, the calcium phosphate powder may have an adequate self-aggregation force, productivity of a layer stack object may be good, and treatability or a handling property may be improved. On the other hand, when the volume average particle diameter Dv is 10.0 µm or less, formation of a thin layer with the layer stack formation powder material results in a thin layer that is filled with the layer stack formation powder material at an adequate filling rate with scarce production of voids, which makes it possible to prevent voids or the like from being produced in a layer stack object to be obtained.

The volume average particle diameter of the layer stack formation powder material can be measured with a publicly-known particle sizing instrument, e.g., MULTISIZER III (manufactured by Coulter Counter Ltd.) and FPIA-3000 (manufactured by Sysmex Corporation) according to a publicly-known method.

A granularity distribution Dv/Dn, which is a ratio of the volume average particle diameter Dv of the layer stack formation powder material to a number average particle diameter Dn thereof is preferably from 1.10 to 1.80, more preferably from 1.10 to 1.40, and yet more preferably from 1.10 to 1.20. When the granularity distribution Dv/Dn is 1.10 or greater, formation of a thin layer with the layer stack formation powder material results in a thin layer that is filled with the layer stack formation powder material at an adequate filling rate with scarce production of voids, which makes it possible to prevent voids or the like from being produced in a layer stack object to be obtained. On the other hand, when the granularity distribution Dv/Dn is 1.80 or less, there are no coarse particles that may become noise in terms of formation of a thin layer of the layer stack formation powder material, and there are few fine particles that may promote self-aggregation excessively.

The granularity distribution Dv/Dn of the layer stack formation powder material can be measured with a publicly-known particle sizing instrument, e.g., MULTISIZER III (manufactured by Coulter Counter Ltd.) and FPIA-3000 (manufactured by Sysmex Corporation) according to a publicly-known method.

The average circularity of the layer stack formation powder material, which is expressed by the formula below, is preferably from 0.70 to 0.80, and more preferably from 0.72 to 0.78.

Average circularity=(perimeter of a circle having the same area as a projected area of the layer stack formation powder material/perimeter of a projected image of the layer stack formation powder material)×100

When the average circularity is 0.70 or greater, the layer stack formation powder material does not aggregate, formation of a thin layer results in a thin layer that is filled with the layer stack formation powder material at an adequate filling rate with scarce production of voids, which makes it possible to prevent voids or the like from being produced in a layer stack object to be obtained. On the other hand, when the average circularity is 0.80 or less, the layer stack formation powder material has an adequate packing property, which makes it easy to remove unhardened powder particles present inside an object obtained, when air-flowing the object after the formation thereof.

The average circularity can be measured with a publicly-known circularity measuring instrument, e.g., FPIA-3000 (manufactured by Sysmex Corporation) according to a publicly-known method.

The layer stack formation powder material of the present invention can be used suitably for simplified efficient formation of various objects or structures, and can be used particularly suitably with the layer stack object formation method and layer stack object formation apparatus of the present invention, which are described below.

(Layer Stack Object Formation Method and Layer Stack Object Formation Apparatus)

A layer stack object formation method of the present invention includes a layer stack formation powder material layer forming step, and a layer hardening step, preferably includes a sintering step, and further includes other steps according to necessity.

A layer stack object formation apparatus used in the present invention includes a layer stack formation powder material layer forming unit, and a layer hardening unit, preferably includes a sintering unit, and further includes other units according to necessity.

The layer stack object formation method of the present invention can be favorably performed with the layer stack object formation apparatus used in the present invention. The layer stack formation powder material layer forming step can be favorably performed by the layer stack formation powder material layer forming unit. The layer hardening step can be favorably performed by the layer hardening unit. The sintering step can be favorably performed by the sintering unit. The other steps can be favorably performed by the other units.

<Layer Stack Formation Powder Material Layer Forming Step and Layer Stack Formation Powder Material Layer Forming Unit>

The layer stack formation powder material layer forming step is a step of forming a layer stack formation powder material layer having a predetermined thickness over a support member, using a layer stack formation powder material containing calcium phosphate.

The layer stack formation powder material layer forming unit is a unit configured to form a layer stack formation powder material layer having a predetermined thickness over a support member, using a layer stack formation powder material containing calcium phosphate.

The powder material may be the layer stack formation powder material of the present invention.

The powder material satisfies A) or B) described below, and a hardened object obtained by hardening the powder material has a hydroxyapatite (HAp) transformation rate of 1% or lower.

A) An organic compound having phosphate group or carboxyl group is imparted over a surface of the calcium phosphate powder, and an imparting amount of the organic compound is 10,000 ppm or lower.

B) The powder material further contains a powder made of an organic compound having phosphate group or carboxyl group, and a mixing amount of the organic compound relative to the calcium phosphate compound is 50% by mass or lower.

<<Support Member>>

The support member is not particularly limited, and an arbitrary support member may be selected according to the purpose as long as the layer stack formation powder material can be mounted over it. Examples thereof include a table having a mounting surface for the layer stack formation powder material, and a base plate of an apparatus described in FIG. 1 of JP-A No. 2000-328106. A surface of the support member, i.e., the mounting surface over which the layer stack formation powder material is mounted may be, for example, a smooth surface or a coarse surface, or may be a flat surface or a curved surface.

—Formation of Layer Stack Formation Powder Material Layer—

A method for placing the layer stack formation powder material over the support member is not particularly limited, and an arbitrary method may be selected according to the purpose. Preferable examples of a method for placing the powder material into, for example, a thin layer include a method involving use of a counter rolling mechanism (a counter roller) or the like, which is used in a selective laser sintering method described in JP-B No. 3607300, a method of spreading the layer stack formation powder material into a thin layer using such a member as a brush, a roller, or a blade, a method of spreading the layer stack formation powder material into a thin layer by pressing the surface of the powder material with a pressing member, and a method involving use of a publicly-known powder layer stack formation apparatus.

For example, in the way described below, the layer stack formation powder material can be placed into a thin layer over the support member, using the counter rolling mechanism (a counter roller), the brush, the blade, or the like, and the pressing member. Specifically, for example, with the counter rolling mechanism (a counter roller), the brush, the blade, or the like, the pressing member, or the like, the layer stack formation powder material is placed over the support member that is disposed within an outer frame (may also be referred to as "mold", "hollow cylinder", "tubular structure", etc.) such that the support member can be lifted up or down while sliding over the inner wall of the outer frame. In this case, when a member that can be lifted up or down within the outer frame is used as the support member, the support member is disposed at a position slightly below the upper end opening of the outer frame, i.e., at a position below the upper end opening by an amount corresponding to the thickness of a layer of the layer stack formation powder material, and then the layer stack formation powder material is placed over the support member. In this way, the layer stack formation powder material can be placed into a thin layer over the support member.

When the powder layer stack formation hardening liquid of the present invention is activated on the layer stack formation powder material placed into a thin layer in this way, the layer is hardened. Then, when the layer stack formation powder material is placed into a thin layer over the hardened thin layer obtained as above in the same manner as described above, and the powder layer stack formation hardening liquid of the present invention is activated on the (layer of) the layer, stack formation powder material placed into the thin layer, hardening occurs. This hardening occurs not only in the (layer of) the layer stack formation powder material placed into the thin layer, but also in the hardened thin layer present below it and obtained in the previous hardening. As a result, a hardened object (a layer stack object, or a hardened object for sintering) having a thickness corresponding to about two layers of the layer stack formation powder material placed into a thin layer is obtained.

Placement of the layer stack formation powder material into a thin layer over the support member can also be performed in an automated manner easily with the publicly-known powder layer stack formation apparatus. Typically, the powder layer stack formation apparatus includes a recoater configured to stack a layer of the layer stack formation powder material, a movable supply tank configured to supply the layer stack formation powder material over the support member, and a movable shaping tank configured for the layer stack formation powder material to be placed into a thin layer and stacked up. In the powder layer stack formation apparatus, it is possible to have the surface of the supply tank positioned slightly above the surface of the shaping tank constantly, by lifting up the supply tank, by lifting down the shaping tank, or by both, it is possible to place the layer stack formation powder material into a thin layer with the recoater actuated from the supply tank side, and it is possible to stack up thin layers of the layer stack formation powder material by repeatedly moving the recoater.

The thickness of the layer stack formation powder material layer is not particularly limited, and may be appropriately selected according to the purpose. However, as the average thickness per layer, it is preferably from 3 μm to 200 μm, and more preferably form 10 μm to 100 μm. When the average thickness is 3 μm or greater, a layer stack object will be obtained in an adequate time, and will not undergo problems of shape collapse or the like during a treatment or handling such as sintering. On the other hand, when the average thickness is 200 μm or less, the dimensional precision of a layer stack object will be good.

The average thickness is not particularly limited, and can be measured according to a publicly-known method.

—Layer Hardening Step and Layer Hardening Unit—

The layer hardening step is a step of delivering the powder layer stack formation hardening liquid of the present invention to the layer stack formation powder material layer and hardening a predetermined region of the layer stack formation powder material layer.

The layer hardening unit is a unit configured to deliver the powder layer stack formation hardening liquid of the present invention to the layer stack formation powder material layer and hardening a predetermined region of the layer stack formation powder material layer.

The hardening liquid may be the powder layer stack formation hardening liquid of the present invention.

The hardening liquid contains at least an organic compound having phosphate group or carboxyl group. The acid value of the organic compound is 0.45 gKOH/g or greater. The content of the organic compound relative to the whole amount of the hardening liquid is 20% by mass or greater.

A method for delivering the powder layer stack formation hardening liquid to the layer stack formation powder material layer is not particularly limited, and an arbitrary method may be selected according to the purpose. Examples thereof include a dispenser method, a spraying method, and an inkjet method. For practicing these methods, a publicly-known apparatus can be favorably used as the layer hardening unit. Among these, the dispenser method is excellent in liquid droplet quantitativity, but has a small coating coverage. The spraying method can form minute discharge droplets easily, has a wide coating coverage and excellent coating performance, but has poor liquid droplet quantitativity, and may have the powder fly away with a spray flow. Therefore, the inkjet method is particularly preferable for the present invention. The inkjet method is preferable in that it is better than the spraying method in liquid droplet quantitativity, has a wider coating coverage than that of the dispenser method, and can form a complex three-dimensional shape precisely and efficiently.

When the inkjet method is employed, the layer hardening unit has a nozzle capable of delivering the powder layer stack formation is hardening liquid to the layer stack formation powder material layer according to the inkjet method. The nozzle is not particularly limited, and a nozzle of a publicly-known inkjet printer can be favorably used. Further, the inkjet printer can be favorably used as the layer hardening unit. Preferable examples of the inkjet printer include SG7100 manufactured by Ricoh Company Limited. The inkjet printer is preferable in that it can perform coating at a high speed, because it can drop a large amount of the powder layer stack formation hardening liquid at a time from the head, with a wide coating coverage.

In the present invention, even when an inkjet printer capable of delivering the powder layer stack formation hardening liquid precisely at a high efficiency is used, the nozzle thereof or the head thereof is not clogged or corroded, because the powder layer stack formation hardening liquid is free from a solid such as particles, and a polymeric high-viscosity material such as a resin. Therefore, there are advantages that the production efficiency of a layer stack object is excellent, and a dimensionally precise cross-linked object with no unexpected volume expansion or the like can be obtained easily, in a short time, and efficiently, because no polymeric compound such as a resin is delivered.

The organic compound having phosphate group or carboxyl group used in the powder layer stack formation hardening liquid tends to exhibit a strong acidity. Typically, a preferably pH is from 5 (weakly acidic) to 12 (basic) in terms of preventing corrosion or clogging of the nozzle head portion of the nozzle used. When a phytic acid is used as the organic compound having phosphate group, corrosion does not occur to the contrary, because phytic acid forms an anticorrosive coating over the surface of a metal such as SUS. Hence, a phytic acid is used favorably as the organic compound having phosphate group.

<Sintering Step and Sintering Unit>

The sintering step is a step of sintering a hardened layer stack object formed by repeating the layer forming step and the layer hardening step sequentially, and is performed by the sintering unit. Through the sintering step, the hardened object can be made into an integrated compact (sintered compact). Examples of the sintering unit include a publicly-known sintering furnace.

The sintering step may be performed not only in the above described manner of performing sintering after a hardened object is obtained, but also in a manner of performing sintering during the stage of stacking the layers of the layer stack formation powder material.

The method for performing sintering during the stage of stacking the layers of the layer stack formation powder material may be a method irradiating the layer stack formation powder material layer with either laser or an electron beam to thereby sinter the layer stack formation powder material layer.

—Laser Irradiation—

The laser of the laser irradiation is not particularly limited, and arbitrary laser may be selected according to the purpose, as long as it is laser in the range of the absorption wavelength of the calcium phosphate powder. Examples thereof include $CO_2$ laser, Nd-YAG laser, fiber laser, and semiconductor laser.

Conditions for the laser irradiation are not particularly limited, and arbitrary conditions may be selected according to the purpose. However, when a small-sized laser is used, in which case, the calcium phosphate powder cannot be melted, it is preferable to mix the calcium phosphate powder with an adhesive (e.g., a polyester-based adhesive), which is to be used in combination, and to melt the adhesive by laser irradiation, to thereby form an object. In this case, $CO_2$ laser is preferable. Preferable irradiation conditions are a laser output of 15 W, a wavelength of 10.6 μm, and a beam diameter of about 0.4 mm.

—Electron Beam Irradiation—

There are not particular limitations to the electron beam, as long as it has energy enough to melt the calcium phosphate powder. Before irradiated with the electron beam, the layer stack formation powder material needs to be treated under vacuum conditions.

Conditions for the electron beam irradiation are not particularly limited, and arbitrary conditions may be selected according to the purpose. However, preferable conditions are an output of 1,500 W, a beam diameter of 0.1 mm, and a degree of vacuum of about $1.0 \times 10^{-5}$ mbar.

<Other Steps and Other Units>

Examples of the other steps include a drying step, a surface protection treatment step, and a painting step.

Examples of the other units include a drying unit, a surface protection treatment unit, and a painting unit.

The drying step is a step of drying a hardened object obtained in the layer hardening step. In this drying step, not only moisture contained in the hardened object, but also an organic substance contained therein may be removed (wax removal). Examples of the drying unit include a publicly-known dryer.

The surface protection treatment step is a step of forming a protection layer over a layer stack object formed in the layer hardening step or the sintering step. By performing this surface protection treatment step, it is possible to provide the surface of the layer stack object with durability that allows the object to be used as is, etc. Examples of the protection layer include a water-fast layer, a weather-fast layer, a lightfast layer, a heat-insulating layer, and a gloss layer. Examples of the surface protection treatment unit include publicly-known surface protection treatment machines, such as a spraying machine and a coating machine.

The painting step is a step of painting the layer stack object. Through the painting step, the layer stack object can be colored in a desired color. Examples of the painting unit include publicly-known painting machines, such as painting machines using spraying, a roller, a brush, or the like.

FIG. 1 shows an example of a powder layer stack formation apparatus used in the present invention. The powder layer stack formation apparatus of FIG. 1 includes a formation-side powder storage tank 1 and a supply-side powder storage tank 2. These powder storage tanks each have a stage 3 capable of moving upward and downward, and are configured to form a layer of the layer stack formation powder material over the stage.

The apparatus includes an inkjet head 5 above the formation-side powder storage tank 1, and a leveling machine 6 (hereinafter may be referred to as recoater). The inkjet head 5 is configured to discharge the powder layer stack formation hardening liquid 4 toward the layer stack formation powder material in the powder storage tank 1. The leveling machine 6 is configured to supply the layer stack formation powder material from the supply-side powder storage tank 2 to the formation-side powder storage tank 1, and to level off the surface of the layer stack formation powder material in the formation-side powder storage tank 1.

The powder layer stack formation hardening liquid 4 is dropped from the inkjet head 5 onto the layer stack formation powder material in the formation-side powder storage tank 1. The position onto which the powder layer stack formation hardening liquid 4 is dropped is determined based on two-dimensional image data (slice data) representing a plurality of planer layers into which a three-dimensional object having a finally desired shape is sliced.

After one layer is printed, the stage 3 of the supply-side powder storage tank 2 is lifted up, and the stage 3 of the formation-side powder storage tank 1 is lifted down, which produces a height difference. An amount of the layer stack formation powder material corresponding to the height difference is moved to the formation-side powder storage tank 1 by the leveling machine 6.

In this way, one new layer stack formation powder material layer is formed over the surface of the layer stack formation powder material layer printed before. The thickness of one powder stacking object formation-purpose powder material layer is from several ten μm to 100 μm.

Printing is performed over the newly formed layer stack formation powder material layer, based on the slice data of the second layer. Through repetition of this process, an object is obtained, and heated and dried with an unillustrated drying unit, to thereby obtain a layer stack object.

Figure 2:
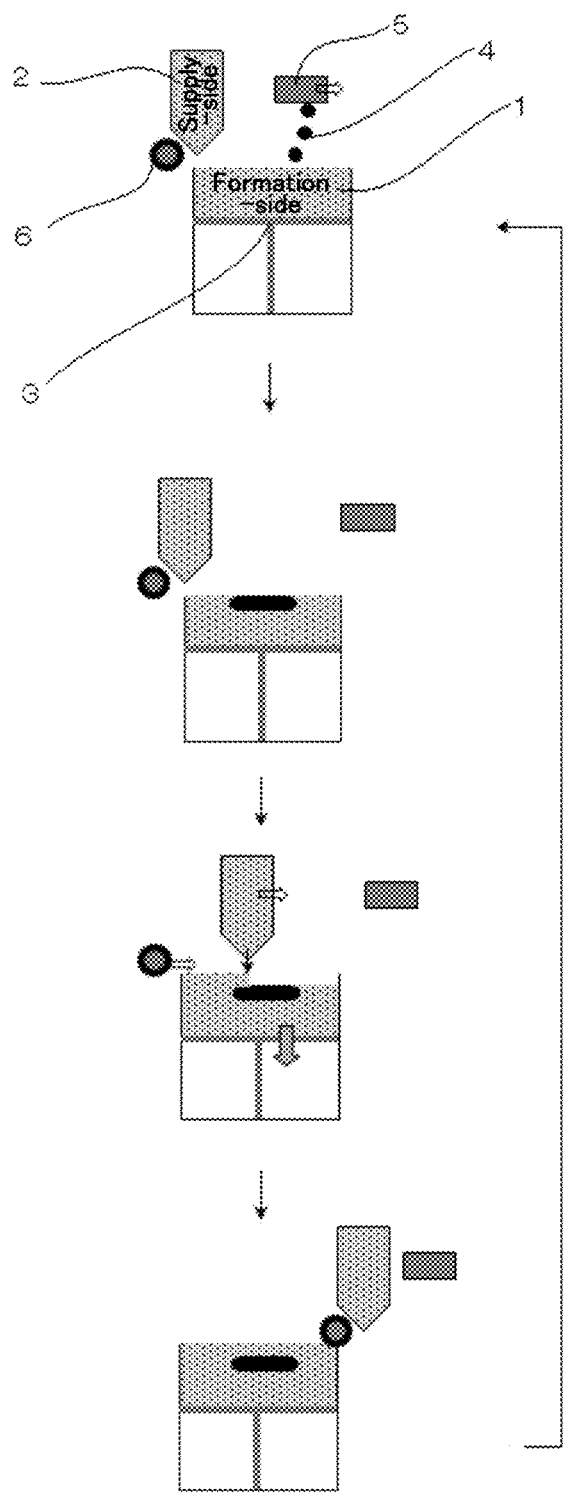
FIG. 2 is a schematic diagram showing another example of a powder layer stack formation apparatus used in the present invention.

FIG. 2 shows another example of a powder layer stack formation apparatus used in the present invention. The powder layer stack formation apparatus of FIG. 2 is identical with that of FIG. 1 in principle, but different in the mechanism for supplying the layer stack formation powder material. Specifically, the supply-side powder storage tank 2 is provided above the formation-side powder storage tank 1. When printing of a first layer is completed, the stage 3 of the formation-side powder storage tank 1 is lifted down by a predetermined amount, and the supply-side powder storage tank 2 moves while dropping a predetermined amount of the layer stack formation powder material onto the formation-side powder storage tank 1, to thereby form a new layer stack formation powder material layer. After this, the leveling machine 6 compresses the layer stack formation powder material layer to a higher bulk density, and levels off the layer stack formation powder material layer to a uniform height at the same time.

The powder layer stack formation apparatus shown in FIG. 2 can be made smaller in size than the configuration of FIG. 1 in which two powder storage tanks are arranged side by side horizontally.

<Layer Stack Object>

A transformation rate of calcium phosphate to hydroxyapatite in the layer stack object is 1% or lower, and preferably 0.5% or lower. When the transformation rate is 1% or lower, calcium phosphate can be prevented from remaining in a living body as hydroxyapatite when the layer stack object is transplanted into the living body.

The transformation rate can be measured with a publicly-known X-ray powder diffractometer according to a publicly-known method. Specifically, crystal phases of the layer stack object are identified before and after the layer stack object is immersed in a SBF (simulated body fluid) for 2 weeks, and from a difference between the rates of areas of peaks specific to hydroxyapatite appearing at 2θ of about 30, a transformation rate can be measured.

The cytotoxicity of the hardened object (layer stack object) can be measured by in-vitro assays including but not limited to: (i) a MTT assay, which is a colorimetric activity assay for measuring an activity of mitochondrial reductase using 3-(4,5-dimethylthiazol-2-yl)-2,5-diphenyltetrazolium bromide tetrazolium salt; (ii) similar assays using any other tetrazolium and a formazan dye, such as XTT and WST assays; (iii) a trypan blue (TB) assay; (iv) a sulforhodamine B (SRB) assay; and (v) a clonogenic capacity assay.

Furthermore, a method known to those skilled in the art for measuring the levels of cellular necrosis and apoptosis may be used for judging whether a cationic lipid or medicine has a cytotoxic activity.

A method for measuring the apoptosis is not particularly limited, and an arbitrary method may be selected according to the purpose. Examples thereof include a TUNEL assay, caspase activity measurement, DNA fragmentation, poly (ADP-ribose)polymerase (PARP) activation, mitochondrial cytochrome C release, apoptosis inducing factor (AIF) transition, and annexin-V staining.

According to the layer stack object formation method and formation apparatus of the present invention, it is possible to form a layer stack object having a complex three-dimensional shape easily, efficiently, without causing a shape collapse before sintering, etc., and dimensionally precisely, using the layer stack formation powder material of the present invention and the layer stack formation material set of the present invention. A layer stack object (hardened object) obtained in this way scarcely transforms to unabsorbable hydroxyapatite when transplanted into a living body, has a high bone inducing ability and a high hardening speed, and besides, has a sufficient strength and an excellent dimensional precision, and can reproduce minute asperity, a curved surface, etc. Therefore, the layer stack object is excellent in aesthetic appearance and quality, and can be favorably used for various applications.

EXAMPLES

Examples of the present invention will be described below. However, the present invention is not limited to these Examples by any means.

Preparation Example A1-1

Preparation of Powder Layer Stack Formation Hardening Liquid A1-1

Water (59.5% by mass), an organic compound having phosphate group, which was a phytic acid (manufactured by Wako Pure Chemical Industries, Ltd., having 6 phosphate groups, and an acid value of 0.74 gKOH/g) (40% by mass), and a surfactant, which was TRITON X-100 (manufactured by Tokyo Chemical Industry Co., Ltd.) (0.5% by mass) were dispersed with a homomixer for 30 minutes, to thereby prepare a powder layer stack formation hardening liquid A1-1.

The viscosity of the obtained powder layer stack formation hardening liquid A1-1 measured in the manner described below was 10 mPa·s at 20° C. The surface tension of the obtained powder layer stack formation hardening liquid A1-1 measured in the manner described below was 24 N/m at 20° C. The acid value of the organic compound having phosphate group or carboxyl group was measured in the manner described below.

<Viscosity>

The viscosity of the powder layer stack formation hardening liquid A1-1 was measured with a B-type rotating viscometer TVB-10M manufactured by Toki Sangyo Co., Ltd. at 25° C.

<Surface Tension>

The surface tension of the powder layer stack formation hardening liquid A1-1 was measured with DY-300 manufactured by Kyowa Interface Science Co., Ltd. at 20° C. according to a Wilhelmy method (Pt plate).

<Acid Value>

The acid value of the organic compound having phosphate group or carboxyl group was measured according to a measurement method described in JIS K0070-1992 under the conditions described below.

Sample preparation: The organic compound (1.0 g) was added in water (100 mL), and stirred and dissolved at room temperature (23° C.) for about 5 minutes, and a small amount of phenolphthalein was added thereto, to thereby obtain a sample solution. A specific calculation method was as follows.

The sample solution was titrated with a previously-standardized N/2 caustic potash or alcohol solution, and the acid value of the sample solution was calculated as follows, based on the amount of the alcoholic potash solution consumed.

Acid value=$KOH$(mL value)×$N$×56.1/mass of sample (where N is a factor of N/2 KOH)

Preparation Example A2-1

Preparation of Layer Stack Formation Powder Material A1-1

Synthesis of Tricalcium Phosphate (α-TCP)

A 0.342 mol/dm$^3$ phosphoric acid aqueous solution was delivered at a speed of 6 mL/min into a 0.513 mol/dm$^3$ calcium hydroxide suspension liquid stirred with a commercially available paddle at 160 rpm, and their pH was stabilized to about 8.7 with ammonia. Then, the resultant was aged with an incubator of 37° C. for 72 hours, filtered, and then dried, to thereby obtain a powder product. Then, the powder product was burned under 800° C. conditions for 1 hour, and then subjected to ball mill pulverization with zirconia beads having a diameter of 3 mm. Here, ball mill pulverization was performed with BM-6 TYPE ROLLER BALL MILL manufactured by Glen Creston Ltd. When 30-minute pulverization was completed, the resultant was filtered through a 75 μm mesh, to thereby obtain minute particles.

Then, the minute particles were burned at 1,400° C. for 5 hours, and then quenched, to thereby obtain an α-tricalcium phosphate (α-TCP) powder, which was a layer stack formation powder material A1-1.

The obtained α-TCP powder as the layer stack formation powder material A1-1 was measured, and as a result, had a volume average particle diameter Dv of 10 μm, a granularity distribution Dv/Dn of 2.38, and an average circularity of 0.782.

<Volume Average Particle Diameter Dv, and Ratio Dv/Dn Between Volume Average Particle Diameter Dv and Number Average Particle Diameter Dn>

COULTER MULTISIZER III (manufactured by Coulter Counter Ltd.) was used as a measuring instrument, and an interface (manufactured by Nikkaki Bios Co., Ltd.) for outputting a number distribution and a volume distribution was connected to a personal computer. Using primary sodium chloride, a 1% by mass NaCl aqueous solution was prepared as an electrolysis solution. The measurement process was performed by adding a surfactant (alkyl benzene sulfonic acid salt) (0.1 mL to 5 mL) as a dispersant, and the layer stack formation powder material (2 mg to 20 mg) into this aqueous solution as the electrolysis solution (100 mL to 150 mL), dispersing them with an ultrasonic disperser for 1 minute to 3 minutes, then pouring the electrolysis aqueous solution (100 mL to 200 mL) into another beaker, adding the obtained sample dispersion liquid into this beaker at a predetermined concentration, and measuring average values of 50,000 particles with COULTER MULTISIZER III described above using a 100 μm aperture. The measurement was performed by dropping the dispersion liquid of the layer stack formation powder material such that the concentration displayed by the measuring instrument would be 8%±2%. The ratio Dv/Dn was calculated based on the obtained volume average particle diameter Dv and the number average particle diameter Dn.

<Average Circularity>

The average circularity was measured with a flow-type particle image analyzer ("FPIA-3000"; manufactured by Sysmex Corporation), and analyzing software (FPIA-3000 DATA PROCESSING PROGRAM FOR FPIA VERSION 00-10). More specifically, a 10% by mass surfactant (alkyl benzene sulfonic acid salt NEOGEN SC-A; manufactured by Dai-ichi Kogyo Seiyaku Co., Ltd.) (0.1 mL to 0.5 mL), and the layer stack formation powder material (0.1 g to 0.5 g) were added into a 100 mL beaker made of glass and mixed with a micro spatula, and then ion-exchanged water (80 mL) was added thereto. The obtained dispersion liquid was dispersed with an ultrasonic disperser (manufactured by Honda Electronics Co., Ltd.) for 3 minutes. Using this dispersion liquid, the shape and distribution of the layer stack formation powder material were measured with FPIA-3000 described above until the concentration became from 5,000 particles/μL to 15,000 particles/μL.

A crystal phase of the prepared calcium phosphate as the layer stack formation powder material A1-1 was identified with an X-ray powder diffractometer (RINT1100 manufactured by Rigaku Corporation) under the conditions described below. As a result, the crystal phase thereof turned out to be α.

[Measurement Conditions]
Vacuum tube: Cu
Voltage: 40 kV
Current: 40 mA
Starting angle: 3°
Ending angle: 80°
Scan speed: 0.5°/min Preparation Example A3-1

Preparation of Layer Stack Formation Powder Material A2-1

Synthesis of Tricalcium Phosphate (β-TCP)

A 0.342 mol/dm$^3$ phosphoric acid aqueous solution was delivered at a speed of 6 mL/min into a 0.513 mol/dm$^3$ calcium hydroxide suspension liquid stirred with a commercially available paddle at 160 rpm, and their pH was stabilized to about 8.7 with ammonia. Then, the resultant was aged with an incubator of 37° C. for 72 hours, filtered, and then dried, to thereby obtain a powder product. Then, the powder product was burned under 800° C. conditions for 1 hour, and then subjected to ball mill pulverization with zirconia beads having a diameter of 3 mm. Here, ball mill pulverization was performed with BM-6 TYPE ROLLER BALL MILL manufactured by Glen Creston Ltd. When 30-minute pulverization was completed, the resultant was filtered through a 75 μm mesh, to thereby obtain minute particles. Then, the minute particles were burned at 1,100° C. for 5 hours, and then quenched, to thereby obtain an β-tricalcium phosphate (β-TCP) powder, which was a layer stack formation powder material A2-1.

The obtained β-TCP powder as the layer stack formation powder material A2-1 was measured in the same manner as in Preparation Example A2-1, and as a result, had a volume average particle diameter Dv of 5 μm, a granularity distribution Dv/Dn of 1.55, and an average circularity of 0.812.

A crystal phase of the obtained layer stack formation powder material A2-1 was identified in the same manner as in Preparation Example A2-1, and as a result, turned out to be β.

Example A1-1

A layer stack object A1-1 was formed in the manner described below, using the layer stack formation powder material A1-1 and powder layer stack formation hardening liquid A1-1 obtained, and a shape printing pattern having a size of 70 mm in length and 12 mm in width.

(1) First, using such a publicly-known powder layer stack formation apparatus as shown in FIG. 1, the layer stack formation powder material A1-1 was delivered from the supply-side powder storage tank to the formation-side powder storage tank, to thereby form a thin layer of the layer stack formation powder material A1-1 having an average thickness of 100 μm over the support member.

(2) Next, using an inkjet printer (SG7100 manufactured by Ricoh Company, Ltd.), the powder layer stack formation hardening liquid A1-1 was delivered (discharged) onto the surface of the formed thin layer of the layer stack formation powder material A1-1 from a nozzle, to capture calcium ions contained in the layer stack formation powder material A1-1 by functioning of the organic compound having phosphate group, to thereby harden the calcium phosphate. The hardening speed of the hardened object was extremely fast. The hardening speed was measured in the manner described below. The result is shown in Table A3.

<Hardening Speed>

A hardening reaction that occurred when the layer stack formation powder material (6 g) and the powder layer stack formation hardening liquid (2 mL) were kneaded was evaluated based on the criteria below.

[Evaluation Criteria]

D: Hardening was insufficient even after 60 seconds or more had passed, with liquidity remaining.

C: Hardening occurred in 15 seconds to 59 seconds but was insufficient, with imperfect shape retention.

B: Hardening occurred in 15 seconds to 59 seconds, with shape retention with no liquidity remaining.

A: Hardening occurred in less than 15 seconds and was sufficient, resulting in a state not easily breakable.

(3) Next, the operations (1) and (2) were repeated up to a predetermined total average thickness of 3 mm, and hardened thin layers of the layer stack formation powder material A1-1 were stacked up sequentially, to thereby form a layer stack object A1-1. The obtained layer stack object A1-1 was air-blown to remove any excess of the layer stack formation powder material, and as a result, did not have a shape collapse. The obtained layer stack object A1-1 was excellent in strength and dimensional precision.

A hydroxyapatite (HAp) transformation rate, cytotoxicity, bone inducing ability, strength (hardness), and dimensional precision of the obtained layer stack object A1-1 were evaluated based on the criteria below. The results are shown in Table A3.

<Hydroxyapatite (HAp) Transformation Rate>

With an X-ray powder diffractometer (RINT1100 manufactured by Rigaku Corporation), crystal phases of the layer stack object A1-1 were identified before and after the layer stack object A1-1 was immersed in a SBF (simulated body fluid) for 2 weeks, and from a difference between the rates of areas of peaks specific to hydroxyapatite appearing at 2θ of about 30, a HAp transformation rate (%) was measured. In the present invention, a HAp transformation rate of 1% or lower is passable.

<Bone Inducing Ability>

Bone inducing ability of the layer stack object A1-1 was evaluated based on the criteria below.

D: When 12 weeks passed after transplantation, there was an undecomposed residue that inhibited bone formation.

C: When 12 weeks passed after transplantation, bone formation was observed, but a mouse could not walk without an external fixator.

B: When 12 weeks passed after transplantation, bone formation was observed, and a mouse could walk without an external fixator.

A: When 8 weeks passed after transplantation, bone formation was observed, and a mouse could walk without an external fixator.

<Cytotoxicity>

About a hundred V79 cells (Chinese hamster lung-derived fibroblasts) were seeded into a cell culture liquid (a 5% by volume fetal calf serum-added MEM culture medium) housed in a well, and kept stationary for 4 hours. After this, the layer stack object A1-1 was put into the well. Culturing was promoted in this state for 1 week. After this, the number of colonies was measured, and an average of the numbers of colonies was calculated. In a similar manner, a control well into which the layer stack object A1-1 was not put was cultured for 1 week, the number of colonies was measured, and an average of the numbers of colonies was calculated. Using these values, a colony formation rate (%) was calculated according to the calculation method below.

Colony formation rate (%)=(average of the numbers of colonies in the culture liquid in which the layer stack object was immersed)/(average of the numbers of colonies in the culture liquid in which the layer stack object was not immersed)×100

It was provided that when the calculated colony formation rate of the layer stack object was 60% or higher, the layer stack object would be judged to have no cytotoxicity.

<Strength (Hardness)>

Strength (hardness) of the layer stack object A1-1 was evaluated based on the criteria below.

D: The layer stack formation powder material was not hardened sufficiently, and the layer stack object could not be taken out and had a state of being unable to retain a predetermined shape if taken out.

C: When the layer stack object was air-blown, the layer stack object itself was also removed slightly in addition to any excess of the layer stack formation powder material, but the layer stack object that was taken out retained its shape.

B: Even when the layer stack object was air-blown, only any excess of the layer stack formation powder material was removed, and the layer stack object that was taken out retained its shape.

A: The layer stack object was hardened sufficiently, and not easily breakable.

Dimensional precision of the layer stack object A1-1 was evaluated based on the criteria below.

D: The obtained layer stack object had distortions over the surface thereof, and when the surface was observed, there were uneven distributions of the layer stack formation powder material and the powder layer stack formation hardening liquid.

C: There were slight distortions and undulations over the surface of the obtained layer stack object.

B: The obtained layer stack object had a favorable surface state, but had slight warping.

A: The obtained layer stack object had a smooth and beautiful surface, and had no warping.

(4) The layer stack object A1-1 obtained in (3) described above was sintered in a sintering furnace under vacuum conditions at 1,300° C. The sintered product of the layer stack object A1-1 was a completely integrated calcium phosphate structure, and had no breakage or the like when slammed to a hard floor.

Example A2-1

A layer stack object A2-1 was formed in the same manner as in Example A1-1, except that unlike in Example A1-1, the content of a phytic acid in the powder layer stack formation hardening liquid was changed to 20% by mass, and glycerin was added in an amount of 40% by mass as a viscosity modifier as shown in Table A1 and Table A2.

The obtained layer stack object A2-1 was evaluated in the same manner as in Example A1-1. The results are shown in Table A3.

Example A3-1

A layer stack object A3-1 was formed in the same manner as in Example A1-1, except that unlike in Example A1-1, the content of a phytic acid in the powder layer stack formation hardening liquid was changed to 50% by mass as shown in Table A1 and Table A2.

The obtained layer stack object A3-1 was evaluated in the same manner as in Example A1-1. The results are shown in Table A3.

Example A4-1

A layer stack object A4-1 was formed in the same manner as in Example A1-1, except that unlike in Example A1-1, the content of the surfactant (TRITON X-100) in the powder layer stack formation hardening liquid was changed to 1.0% by mass as shown in Table A1 and Table A2.

The obtained layer stack object A4-1 was evaluated in the same manner as in Example A1-1. The results are shown in Table A3.

Example A5-1

A layer stack object A5-1 was formed in the same manner as in Example A1-1, except that unlike in Example A1-1, the content of a phytic acid was changed to 25% by mass to thereby change the viscosity of the powder layer stack formation hardening liquid at 20° C. to 5 mPa·s as shown in Table A1 and Table A2.

The obtained layer stack object A5-1 was evaluated in the same manner as in Example A1-1. The results are shown in Table A3.

Example A6-1

A layer stack object A6-1 was formed in the same manner as in Example A1-1, except that unlike in Example A1-1, a viscosity modifier (glycerin) was added in an amount of 20% by mass in the powder layer stack formation hardening liquid to thereby change the viscosity of the powder layer stack formation hardening liquid at 20° C. to 20 mPa·s as shown in Table A1 and Table A2.

The obtained layer stack object A6-1 was evaluated in the same manner as in Example A1-1. The results are shown in Table A3.

Example A7-1

A layer stack object A7-1 was formed in the same manner as in Example A1-1, except that unlike in Example A1-1, the additive amount of the surfactant (TRITON X-100) was changed to 0.4% by mass to thereby change the surface tension of the powder layer stack formation hardening liquid to 30 N/m as shown in Table A1 and Table A2.

The obtained layer stack object A7-1 was evaluated in the same manner as in Example A1-1. The results are shown in Table A3.

Example A8-1

A layer stack object A8-1 was formed in the same manner as in Example A1-1, except that unlike in Example A1-1, the content of the surfactant (TRITON X-100) in the powder layer stack formation hardening liquid was changed to 1.1% by mass as shown in Table A1 and Table A2.

The obtained layer stack object A8-1 was evaluated in the same manner as in Example A1-1. The results are shown in Table A3.

Example A9-1

A layer stack object A9-1 was formed in the same manner as in Example A1-1, except that the surfactant (TRITON X-100) used in Example A1-1 in the powder layer stack formation hardening liquid was changed to sodium cholate (solid, manufactured by Tokyo Chemical Industry Co., Ltd.) as shown in Table A1 and Table A2.

The obtained layer stack object A9-1 was evaluated in the same manner as in Example A1-1. The results are shown in Table A3.

Example A10-1

A layer stack object A10-1 was formed in the same manner as in Example A1-1, except that unlike in Example A1-1, the content of a phytic acid was changed to 20% by mass to thereby change the viscosity of the powder layer stack formation hardening liquid at 20° C. to 4 mPa·s as shown in Table A1 and Table A2.

The obtained layer stack object A10-1 was evaluated in the same manner as in Example A1-1. The results are shown in Table A3.

Example A11-1

A layer stack object A11-1 was formed in the same manner as in Example A1-1, except that unlike in Example A1-1, a viscosity modifier (glycerin) was added in an amount of 25% by mass in the powder layer stack formation hardening liquid to thereby change the viscosity of the powder layer stack formation hardening liquid at 20° C. to 21 mPa·s as shown in Table A1 and Table A2.

The obtained layer stack object A11-1 was evaluated in the same manner as in Example A1-1. The results are shown in Table A3.

Example A12-1

A layer stack object A12-1 was formed in the same manner as in Example A1-1, except that unlike in Example A1-1, the additive amount of the surfactant (TRITON X-100) was changed to 0.3% by mass to thereby change the surface tension of the powder layer stack formation hardening liquid to 31 N/m as shown in Table A1 and Table A2.

The obtained layer stack object A12-1 was evaluated in the same manner as in Example A1-1. The results are shown in Table A3.

Example A13-1

A layer stack object A13-1 was formed in the same manner as in Example A1-1, except that α-tricalcium phosphate (α-TCP) used in Example A1-1 was changed to β-tricalcium phosphate (β-TCP), which was the layer stack formation powder material A2-1 of Preparation Example A3-1 as shown in Table A2.

The obtained layer stack object A13-1 was evaluated in the same manner as in Example A1-1. The results are shown in Table A3.

Comparative Example A1-1

A layer stack object A14-1 was formed in the same manner as in Example A1-1, except that unlike in Example A1-1, the content of a phytic acid in the powder layer stack formation hardening liquid was changed to 19% by mass as shown in Table A1 and Table A2.

The obtained layer stack object A14-1 was evaluated in the same manner as in Example A1-1. The results are shown in Table A3.

Comparative Example A2-1

A layer stack object A15-1 was formed in the same manner as in Example A1-1, except that unlike in Example A1-1, no organic compound having phosphate group was added in the powder layer stack formation hardening liquid as shown in Table A1 and Table A2.

The obtained layer stack object A15-1 was evaluated in the same manner as in Example A1-1. The results are shown in Table A3.

Comparative Example A3-1

A layer stack object A16-1 was formed in the same manner as in Example A1-1, except that 40% by mass of phytic acid used in Example A1-1 was changed to 21% by mass of inositol trisphosphate (manufactured by Dojindo Laboratories, Co., Ltd., having 3 phosphate groups, and an acid value of 0.41 gKOH/g) as shown in Table A1 and Table A2.

The obtained layer stack object A16-1 was evaluated in the same manner as in example A1-1. The results are shown in Table A3.

TABLE A1

| | Powder layer stack formation hardening liquid | | | | | | |
|---|---|---|---|---|---|---|---|
| | Organic compound having phosphate group | | | | surfactant | | |
| | Kind | Acid value (gKOH/g) | Number of phosphate groups | Content (% by mass) | Kind | State (20° C.) | Content (% by mass) |
| Ex. A1-1 | Phytic acid | 0.74 | 6 | 40 | TRITON X-100 | Liquid | 0.5 |
| Ex. A2-1 | Phytic acid | 0.74 | 6 | 20 | TRITON X-100 | Liquid | 0.5 |
| Ex. A3-1 | Phytic acid | 0.74 | 6 | 50 | TRITON X-100 | Liquid | 0.5 |
| Ex. A4-1 | Phytic acid | 0.74 | 6 | 40 | TRITON X-100 | Liquid | 1.0 |
| Ex. A5-1 | Phytic acid | 0.74 | 6 | 25 | TRITON X-100 | Liquid | 0.5 |
| Ex. A6-1 | Phytic acid | 0.74 | 6 | 40 | TRITON X-100 | Liquid | 0.5 |
| Ex. A7-1 | Phytic acid | 0.74 | 6 | 40 | TRITON X-100 | Liquid | 0.4 |
| Ex. A8-1 | Phytic acid | 0.74 | 6 | 40 | TRITON X-100 | Liquid | 1.1 |
| Ex. A9-1 | Phytic acid | 0.74 | 6 | 40 | Sodium cholate | Solid | 0.5 |
| Ex. A10-1 | Phytic acid | 0.74 | 6 | 20 | TRITON X-100 | Liquid | 0.5 |
| Ex. A11-1 | Phytic acid | 0.74 | 6 | 40 | TRITON X-100 | Liquid | 0.5 |
| Ex. A12-1 | Phytic acid | 0.74 | 6 | 40 | TRITON X-100 | Liquid | 0.3 |
| Ex. A13-1 | Phytic acid | 0.74 | 6 | 40 | TRITON X-100 | Liquid | 0.5 |
| Comp. Ex. A1-1 | Phytic acid | 0.74 | 6 | 19 | TRITON X-100 | Liquid | 0.5 |

TABLE A1-continued

| | Powder layer stack formation hardening liquid | | | | | |
|---|---|---|---|---|---|---|
| | Organic compound having phosphate group | | | surfactant | | |
| | Kind | Acid value (gKOH/g) | Number of phosphate groups | Content (% by mass) | Kind | State (20° C.) | Content (% by mass) |
| Comp. Ex. A2-1 | None | — | — | — | TRITON X-100 | Liquid | 0.5 |
| Comp. Ex. A3-1 | Inositol tris-phosphate | 0.41 | 3 | 21 | TRITON X-100 | Liquid | 0.5 |

TABLE A2

| | Powder layer stack formation hardening liquid | | | | |
|---|---|---|---|---|---|
| | Aqueous medium Water content (% by mass) | Viscosity modifier Glycerin content (% by mass) | Viscosity (mPa·s) | Surface tension (N/m) | Kind of calcium phosphate powder |
| Ex. A1-1 | 59.5 | — | 10 | 24 | α-TCP |
| Ex. A2-1 | 39.5 | 40 | 6 | 26 | α-TCP |
| Ex. A3-1 | 49.5 | — | 17 | 23 | α-TCP |
| Ex. A4-1 | 59.0 | — | 11 | 18 | α-TCP |
| Ex. A5-1 | 74.5 | — | 5 | 25 | α-TCP |
| Ex. A6-1 | 39.5 | 20 | 20 | 24 | α-TCP |
| Ex. A7-1 | 59.6 | — | 13 | 30 | α-TCP |
| Ex. A8-1 | 58.9 | — | 9 | 17 | α-TCP |
| Ex. A9-1 | 59.5 | — | 11 | 30 | α-TCP |
| Ex. A10-1 | 79.5 | — | 4 | 22 | α-TCP |
| Ex. A11-1 | 34.5 | 25 | 21 | 23 | α-TCP |
| Ex. A12-1 | 59.7 | — | 12 | 31 | α-TCP |
| Ex. A13-1 | 59.5 | — | 10 | 24 | β-TCP |
| Comp. Ex. A1-1 | 80.5 | — | 6 | 26 | α-TCP |
| Comp. Ex. A2-1 | 99.5 | — | 2 | 25 | α-TCP |
| Comp. Ex. A3-1 | 78.5 | — | 6 | 27 | α-TCP |

TABLE A3

| | HAp transformation rate (%) | Cyto-toxicity | Bone inducing ability | Hardening Strength | Hardening speed | Dimensional precision |
|---|---|---|---|---|---|---|
| Ex. A1-1 | 0.1 | Absent | B | A | A | A |
| Ex. A2-1 | 0.9 | Absent | C | B | B | B |
| Ex. A3-1 | 0.1 | Absent | B | A | A | B |
| Ex. A4-1 | 0.1 | Absent | B | A | A | A |
| Ex. A5-1 | 0.1 | Absent | B | A | A | B |
| Ex. A6-1 | 0.1 | Absent | B | A | A | B |
| Ex. A7-1 | 0.1 | Absent | B | A | A | B |
| Ex. A8-1 | 0.1 | Absent | B | A | A | B |
| Ex. A9-1 | 0.1 | Absent | B | A | A | B |
| Ex. A10-1 | 0.1 | Absent | B | B | B | A |
| Ex. A11-1 | 0.1 | Absent | B | A | A | B |
| Ex. A12-1 | 0.1 | Absent | B | A | A | B |
| Ex. A13-1 | 0.1 | Absent | B | B | B | B |
| Comp. Ex. A1-1 | 1.1 | Absent | D | D | D | B |
| Comp. Ex. A2-1 | 16.4 | Absent | D | D | D | A |
| Comp. Ex. A3-1 | 1 | Absent | D | D | D | C |

From the results of Table A3, Comparative Examples A1-1 and A2-1 both had a HAp transformation rate of higher than 1%, and when transplanted into a living body, would have a trouble of transforming to hydroxyapatite (HAp) and remaining in the living body.

Preparation Example A1-2

Preparation of Powder Layer Stack Formation Hardening Liquid A1-2

Water (59.2% by mass), an organic compound having phosphate group, which was a phytic acid having an acid value of 0.74 gKOH/g (manufactured by Wako Pure Chemical Industries, Ltd., having 6 phosphate groups) (40% by mass), a silicone antifoaming agent, which was KM-72F (manufactured by Shin-Etsu Chemical Co., Ltd., with a silica volume average particle diameter of 7.4 μm) (0.3% by mass), and a surfactant, which was TRITON X-100 (manufactured by Tokyo Chemical Industry Co., Ltd.) (0.5% by mass) were dispersed with a homomixer for 30 minutes, to thereby prepare a powder layer stack formation hardening liquid A1-2.

The viscosity of the obtained powder layer stack formation hardening liquid A1-2 measured in the same manner as in Preparation Example A1-1 was 10 mPa·s at 20° C. The surface tension of the obtained powder layer stack formation hardening liquid A1-2 measured in the same manner as in Preparation Example A1-1 was 24 N/m at 20° C. The volume average particle diameter of silica contained in the silicone antifoaming agent was measured with MICROTRACK UPA (manufactured by Microtrack Co., Ltd.).

Example A1-2

A layer stack object A1-2 was formed in the manner described below, using the layer stack formation powder material A1-1 prepared in Preparation Example A2-1 and the powder layer stack formation hardening liquid A1-2, and a shape printing pattern having a size of 70 mm in length and 12 mm in width.

(1) First, using such a publicly-known powder layer stack formation apparatus as shown in FIG. 1, the layer stack formation powder material A1-1 was delivered from the supply-side powder storage tank to the formation-side powder storage tank, to thereby form a thin layer of the layer stack formation powder material A1-1 having an average thickness of 100 μm over the support member.

(2) Next, using an inkjet printer (SG7100 manufactured by Ricoh Company, Ltd.), the powder layer stack formation hardening liquid A1-2 was delivered (discharged) onto the surface of the formed thin layer of the layer stack formation powder material A1-1 from a nozzle, to capture calcium ions contained in the layer stack formation powder material A1-1 by functioning of the organic compound having phosphate group or carboxyl group, to thereby harden the calcium phosphate. The hardening speed of the hardened object was extremely fast. The hardening speed was measured in the sane manner as in Example A1-1. The result is shown in Table 6.

(3) Next, the operations (1) and (2) were repeated up to a predetermined total average thickness of 3 mm, and hardened thin layers of the layer stack formation powder material A1-1 were stacked up sequentially, to thereby form a layer stack object A1-2. The obtained layer stack object A1-2 was air-blown to remove any excess of the layer stack formation powder material A1-1, and as a result, did not have a shape collapse. The obtained layer stack object A1-2 was excellent in strength and dimensional precision.

A hydroxyapatite (HAp) transformation rate, cytotoxicity, bone inducing ability, strength (hardness), and dimensional precision of the obtained layer stack object A1-2 were evaluated in the same manner as in Example A1-1. The results are shown in Table A6.

(4) The layer stack object A1-2 obtained in (3) was sintered in a sintering furnace under vacuum conditions at 1,300° C. The sintered product of the layer stack object A1-2 was a completely integrated calcium phosphate structure, and had no breakage or the like when slammed to a hard floor.

Example A2-2

A layer stack object A2-2 was formed in the same manner as in Example A1-2, except that unlike in Example A1-2, the content of a phytic acid in the powder layer stack formation hardening liquid was changed to 20% by mass, and glycerin was added in an amount of 40% by mass as a viscosity modifier as shown in Table A4 and Table A5.

The obtained layer stack object A2-2 was evaluated in the same manner as in Example A1-2. The results are shown in Table A6.

Example A3-2

A layer stack object A3-2 was formed in the same manner as in Example A1-2, except that a phytic acid used in the powder layer stack formation hardening liquid in Example A1-2 was changed to an etidronic acid (manufactured by Dojindo Laboratories, Co., Ltd., having 2 phosphate groups, and an acid value of 0.51 gKOH/g) as shown in Table A4 and Table A5.

The obtained layer stack object A3-2 was evaluated in the same manner as in Example A1-2. The results are shown in Table A6.

Example A4-2

A layer stack object A4-2 was formed in the same manner as in Example A1-2, except that unlike in Example A1-2, the content of the surfactant (TRITON X-100) in the powder layer stack formation hardening liquid was changed to 1.0% by mass as shown in Table A4 and Table A5.

The obtained layer stack object A4-2 was evaluated in the same manner as in Example A1-2. The results are shown in Table A6.

Example A5-2

A layer stack object A5-2 was formed in the same manner as in Example A1-2, except that unlike in Example A1-2, the content of a phytic acid was changed to 25% by mass to thereby change the viscosity of the powder layer stack formation hardening liquid at 20° C. to 5 mPa·s as shown in Table A4 and Table A5.

The obtained layer stack object A5-2 was evaluated in the same manner as in Example A1-2. The results are shown in Table A6.

Example A6-2

A layer stack object A6-2 was formed in the same manner as in Example A1-2, except that unlike in Example A1-2, a viscosity modifier (glycerin) was added in an amount of 20% by mass in the powder layer stack formation hardening liquid to thereby change the viscosity of the powder layer stack formation hardening liquid at 20° C. to 20 mPa·s as shown in Table A4 and Table A5.

The obtained layer stack object A6-2 was evaluated in the same manner as in Example A1-2. The results are shown in Table A6.

Example A7-2

A layer stack object A7-2 was formed in the same manner as in example A1-2, except that unlike in Example A1-2, the additive amount of the surfactant (TRITON X-100) was changed to 0.4% by mass to thereby change the surface tension to 30 N/m as shown in Table A4 and Table A5.

The obtained layer stack object A7-2 was evaluated in the same manner as in example A1-2. The results are shown in Table A6.

Example A8-2

A layer stack object A8-2 was formed in the same manner as in Example A1-2, except that 40% by mass of phytic acid used in Example A1-2 was changed to 40% by mass of citric acid (manufactured by Wako Pure Chemical Industries, Ltd., having 3 carboxyl groups, and an acid value of 0.89 gKOH/g) as shown in Table A4 and Table A5.

The obtained layer stack object A8-2 was evaluated in the same manner as in Example A1-2. The results are shown in Table A6.

Example A9-2

A layer stack object A9-2 was formed in the same manner as in Example A1-2, except that unlike in Example A1-2, the content of the surfactant (TRITON X-100) in the powder layer stack formation hardening liquid was changed to 1.1% by mass as shown in Table A4 and Table A5.

The obtained layer stack object A9-2 was evaluated in the same manner as in Example A1-2. The results are shown in Table A6.

Example A10-2

A layer stack object A10-2 was formed in the same manner as in Example A1-2, except that the surfactant (TRITON X-100) used in the powder layer stack formation hardening liquid in Example A1-2 was changed to sodium cholate (solid, manufactured by Tokyo Chemical Industry Co., Ltd.) as shown in Table A4 and Table A5.

The obtained layer stack object A10-2 was evaluated in the same manner as in Example A1-2. The results are shown in Table A6.

Example A11-2

A layer stack object A11-2 was formed in the same manner as in Example A1-2, except that unlike in Example A1-2, the content of a phytic acid was changed to 20% by mass to thereby change the viscosity of the powder layer stack formation hardening liquid at 20° C. to 4 mPa·s as shown in Table A4 and Table A5.

The obtained layer stack object A11-2 was evaluated in the same manner as in Example A1-2. The results are shown in Table A6.

Example A12-2

A layer stack object A12-2 was formed in the same manner as in Example A1-2, except that unlike in Example A1-2, a viscosity modifier (glycerin) was added in an amount of 25% by mass in the powder layer stack formation hardening liquid to thereby change the viscosity of the powder layer stack formation hardening liquid at 20° C. to 21 mPa·s as shown in Table A4 and Table A5.

The obtained layer stack object A12-2 was evaluated in the same manner as in Example A1-2. The results are shown in Table A6.

Example A13-2

A layer stack object A13-2 was formed in the same manner as in Example A1-2, except that unlike in Example A1-2, the additive amount of the surfactant TRITON X-100 was changed to 0.3% by mass to thereby change the surface tension to 31 N/m as shown in Table A4 and Table A5.

The obtained layer stack object A13-2 was evaluated in the same manner as in Example A1-2. The results are shown in Table A6.

Example A14-2

A layer stack object A14-2 was formed in the same manner as in Example A1-2, except that α-tricalcium phosphate (α-TCP) used in Example A1-2 was changed to β-tricalcium phosphate (β-TCP), which was the layer stack formation powder material A2-1 prepared in Preparation Example A3-1, as shown in Table A5.

The obtained layer stack object A14-2 was evaluated in the same manner as in Example A1-2. The results are shown in Table A6.

Example A15-2

A layer stack object A15-2 was formed in the same manner as in Example A1-2, except that unlike in Example A1-2, the additive amount of the silicone antifoaming agent KM-72F was changed to 0.005% by mass as shown in Table A4 and Table A5.

The obtained layer stack object A15-2 was evaluated in the same manner as in Example A1-2. The results are shown in Table A6.

Example A16-2

A layer stack object A16-2 was formed in the same manner as in Example A1-2, except that unlike in example A1-2, the additive amount of the silicone antifoaming agent KM-72F was changed to 3% by mass as shown in Table A4 and Table A5.

The obtained layer stack object A16-2 was evaluated in the same manner as in Example A1-2. The results are shown in Table A6.

Example A17-2

A layer stack object A17-2 was formed in the same manner as in example A1-2, except that the silicone antifoaming agent KM-72F used in Example A1-2 was changed to a silicone antifoaming agent KM-73 (manufactured by Shin-Etsu Chemical Col., Ltd. having a silica volume average particle diameter of 10.6 μm) as shown in Table A4 and Table A5.

The obtained layer stack object A17-2 was evaluated in the same manner as in example A1-2. The results are shown in Table A6.

Comparative Example A1-2

A layer stack object A18-2 was formed in the same manner as in Example A1-2, except that unlike in Example A1-2, the content of a phytic acid in the powder layer stack formation hardening liquid was changed to 19% by mass as shown in Table A4 and Table A5.

The obtained layer stack object A18-2 was evaluated in the same manner as in Example A1-2. The results are shown in Table A6.

Comparative Example A2-2

A layer stack object A19-2 was formed in the same manner as in Example A3-2, except unlike in Example A3-2, the content of the etidronic acid in the powder layer stack formation hardening liquid was changed to 19% by mass as shown in Table A4 and Table A5.

The obtained layer stack object A19-2 was evaluated in the same manner as in Example A1-2. The results are shown in Table A6.

Comparative example A3-2

A layer stack object A20-2 was formed in the same manner as in Example A1-2, except that unlike in Example A1-2, no organic compound having phosphate group or carboxyl group was added in the powder layer stack formation hardening liquid as shown in Table A4 and Table A5.

The obtained layer stack object A20-2 was evaluated in the same manner as in Example A1-2. The results are shown in Table A6.

Comparative Example A4-2

A layer stack object A21-2 was formed in the same manner as in Example A1-2, except that a phytic acid having phosphate group, which was used in the powder layer stack formation hardening liquid in Example A1-2 was changed to sphingosine-1-phosphate (manufactured by Wako Pure Chemical Industries, Ltd., having 1 phosphate group, and an acid value of 0.18 gKOH/g) as shown in Table A4 and Table A5.

The obtained layer stack object A21-2 was evaluated in the same manner as in Example A1-2. The results are shown in Table A6.

TABLE A4

Powder layer stack formation hardening liquid

| | Organic compound having phosphate or carboxyl group | | | | Surfactant | | |
|---|---|---|---|---|---|---|---|
| | | Acid | | | | | |
| | Kind | value (gKOH/g) | Number of phosphate groups | Number of carboxyl groups | Content (% by mass) | Kind | State (20° C.) | Content (% by mass) |

| | Kind | Acid value (gKOH/g) | Number of phosphate groups | Number of carboxyl groups | Content (% by mass) | Kind | State (20° C.) | Content (% by mass) |
|---|---|---|---|---|---|---|---|---|
| Ex. A1-2 | Phytic acid | 0.74 | 6 | — | 40 | TRITON X-100 | Liquid | 0.5 |
| Ex. A2-2 | Phytic acid | 0.74 | 6 | — | 20 | TRITON X-100 | Liquid | 0.5 |
| Ex. A3-2 | Etidronic acid | 0.51 | 2 | — | 40 | TRITON X-100 | Liquid | 0.5 |
| Ex. A4-2 | Phytic acid | 0.74 | 6 | — | 40 | TRITON X-100 | Liquid | 1.0 |
| Ex. A5-2 | Phytic acid | 0.74 | 6 | — | 25 | TRITON X-100 | Liquid | 0.5 |
| Ex. A6-2 | Phytic acid | 0.74 | 6 | — | 40 | TRITON X-100 | Liquid | 0.5 |
| Ex. A7-2 | Phytic acid | 0.74 | 6 | — | 40 | TRITON X-100 | Liquid | 0.4 |
| Ex. A8-2 | Citric acid | 0.89 | — | 3 | 40 | TRITON X-100 | Liquid | 0.5 |
| Ex. A9-2 | Phytic acid | 0.74 | 6 | — | 40 | TRITON X-100 | Liquid | 1.1 |
| Ex. A10-2 | Phytic acid | 0.74 | 6 | — | 40 | Sodium cholate | Solid | 0.5 |
| Ex. A11-2 | Phytic acid | 0.74 | 6 | — | 20 | TRITON X-100 | Liquid | 0.5 |
| Ex. A12-2 | Phytic acid | 0.74 | 6 | — | 40 | TRITON X-100 | Liquid | 0.5 |
| Ex. A13-2 | Phytic acid | 0.74 | 6 | — | 40 | TRITON X-100 | Liquid | 0.3 |
| Ex. A14-2 | Phytic acid | 0.74 | 6 | — | 40 | TRITON X-100 | Liquid | 0.5 |
| Ex. A15-2 | Phytic acid | 0.74 | 6 | — | 40 | TRITON X-100 | Liquid | 0.5 |
| Ex A16-2 | Phytic acid | 0.74 | 6 | — | 40 | TRITON X-100 | Liquid | 0.5 |
| Ex. A17-2 | Phytic acid | 0.74 | 6 | — | 40 | TRITON X-100 | Liquid | 0.5 |
| Comp. Ex. A1-2 | Phytic acid | 0.74 | 6 | — | 19 | TRITON X-100 | Liquid | 0.5 |
| Comp. Ex. A2-2 | Etidronic acid | 0.51 | 2 | — | 19 | TRITON X-100 | Liquid | 0.5 |
| Comp. Ex. A3-2 | None | — | — | — | — | TRITON X-100 | Liquid | 0.5 |
| Comp. Ex. A4-2 | Sphingosine-1-phosphate | 0.18 | 1 | — | 40 | TRITON X-100 | Liquid | 0.5 |

TABLE A5

Powder layer stack formation hardening liquid

| | Antifoaming agent | | | Aqueous medium | Viscosity modifier | | | |
|---|---|---|---|---|---|---|---|---|
| | Kind | Vol. ave. particle diameter of inorganic particles (μm) | Content (% by mass) | Water content (% by mass) | Glycerin content (% by mass) | Viscosity (mPa·s) | Surface tension (N/m) | Kind of calcium phosphate powder |
| Ex. A1-2 | KM-72F | 7.4 | 0.3 | 59.2 | — | 10 | 24 | α-TCP |
| Ex. A2-2 | KM-72F | 7.4 | 0.3 | 39.2 | 40 | 6 | 26 | α-TCP |
| Ex. A3-2 | KM-72F | 7.4 | 0.3 | 59.2 | — | 7 | 23 | α-TCP |
| Ex. A4-2 | KM-72F | 7.4 | 0.3 | 58.7 | — | 11 | 18 | α-TCP |
| Ex. A5-2 | KM-72F | 7.4 | 0.3 | 74.2 | — | 5 | 25 | α-TCP |
| Ex. A6-2 | KM-72F | 7.4 | 0.3 | 39.2 | 20 | 20 | 24 | α-TCP |
| Ex. A7-2 | KM-72F | 7.4 | 0.3 | 59.3 | — | 13 | 30 | α-TCP |
| Ex. A8-2 | KM-72F | 7.4 | 0.3 | 59.2 | — | 12 | 28 | α-TCP |
| Ex. A9-2 | KM-72F | 7.4 | 0.3 | 58.6 | — | 11 | 14 | α-TCP |
| Ex. A10-2 | KM-72F | 7.4 | 0.3 | 59.2 | — | 10 | 29 | α-TCP |
| Ex. A11-2 | KM-72F | 7.4 | 0.3 | 79.2 | — | 4 | 27 | α-TCP |
| Ex. A12-2 | KM-72F | 7.4 | 0.3 | 34.2 | 25 | 21 | 25 | α-TCP |
| Ex. A13-2 | KM-72F | 7.4 | 0.3 | 59.4 | — | 12 | 31 | α-TCP |
| Ex. A14-2 | KM-72F | 7.4 | 0.3 | 59.2 | — | 10 | 24 | β-TCP |

TABLE A5-continued

| | Powder layer stack formation hardening liquid | | | | | | |
|---|---|---|---|---|---|---|---|
| | Antifoaming agent | | | Aqueous medium | Viscosity modifier | | |
| | Kind | Vol. ave. particle diameter of inorganic particles (μm) | Content (% by mass) | Water content (% by mass) | Glycerin content (% by mass) | Viscosity (mPa·s) | Surface tension (N/m) | Kind of calcium phosphate powder |
| Ex. A15-2 | KM-72F | 7.4 | 0.005 | 59.495 | — | 11 | 27 | α-TCP |
| Ex A16-2 | KM-72F | 7.4 | 3 | 56.5 | — | 19 | 20 | α-TCP |
| Ex. A17-2 | KM-73 | 10.6 | 0.3 | 59.2 | — | 9.6 | 28 | α-TCP |
| Comp. Ex. A1-2 | KM-72F | 7.4 | 0.3 | 80.2 | — | 6 | 26 | α-TCP |
| Comp. Ex. A2-2 | KM-72F | 7.4 | 0.3 | 80.2 | — | 3 | 21 | α-TCP |
| Comp. Ex. A3-2 | KM-72F | 7.4 | 0.3 | 99.2 | — | 2 | 25 | α-TCP |
| Comp. Ex. A4-2 | KM-72F | 7.4 | 0.3 | 59.2 | — | 7 | 26 | α-TCP |

TABLE A6

| | HAp transformation rate (%) | Cytotoxicity | Bone inducing ability | Strength | Hardening speed | Dimensional precision |
|---|---|---|---|---|---|---|
| Ex. A1-2 | 0.1 | Absent | A | A | A | A |
| Ex. A2-2 | 0.8 | Absent | A | B | B | B |
| Ex. A3-2 | 0.1 | Absent | A | B | B | B |
| Ex. A4-2 | 0.1 | Absent | A | A | A | A |
| Ex. A5-2 | 0.1 | Absent | A | A | A | B |
| Ex. A6-2 | 0.1 | Absent | A | A | A | B |
| Ex. A7-2 | 0.1 | Absent | A | A | A | B |
| Ex. A8-2 | 0.1 | Absent | A | B | B | A |
| Ex. A9-2 | 0.1 | Absent | A | B | B | B |
| Ex. A10-2 | 0.1 | Absent | A | B | B | B |
| Ex. A11-2 | 0.1 | Absent | A | B | B | B |
| Ex. A12-2 | 0.1 | Absent | A | B | B | B |
| Ex. A13-2 | 0.1 | Absent | A | A | A | B |
| Ex. A14-2 | 0.1 | Absent | A | B | B | B |
| Ex. A15-2 | 0.1 | Absent | A | A | A | A |
| Ex A16-2 | 0.1 | Absent | A | A | A | A |
| Ex. A17-2 | 0.1 | Absent | A | C | B | C |
| Comp. Ex. A1-2 | 1.1 | Absent | A | D | D | B |
| Comp. Ex. A2-2 | 0.1 | Absent | A | D | D | D |
| Comp. Ex. A3-2 | 16.4 | Absent | A | D | D | A |
| Comp. Ex. A4-2 | 11.2 | Absent | A | B | B | D |

From the results of Table A6, Comparative Example A1-2, Comparative Example A3-2, and Comparative Example A4-2 had a HAp transformation rate of higher than 1%, and when transplanted into a living body, would have a trouble of transforming to hydroxyapatite (HAp) and remaining in the living body.

Preparation Example B1

Preparation of Layer Stack Formation Powder Material B1

Synthesis of α-Tricalcium Phosphate (α-TCP)

A 0.342 mol/dm$^3$ phosphoric acid aqueous solution was delivered at a speed of 6 mL/min into a 0.513 mol/dm$^3$ calcium hydroxide suspension liquid stirred with a commercially available paddle at 160 rpm, and their pH was stabilized to about 8.7 with ammonia. Then, the resultant was aged with an incubator of 37° C. for 72 hours, filtered, and then dried, to thereby obtain a powder product. Then, the powder product was burned under 800° C. conditions for 1 hour, and then subjected to ball mill pulverization with zirconia beads having a diameter of 3 mm. Here, ball mill pulverization was performed with BM-6 TYPE ROLLER BALL MILL manufactured by Glen Creston Ltd. When 30-minute pulverization was completed, the resultant was filtered through a 75 μm mesh, to thereby obtain minute particles. Then, the minute particles were burned at 1,400° C. for 5 hours, and then quenched, to thereby obtain an α-tricalcium phosphate (α-TCP) powder.

The obtained α-TCP powder was measured in the same manner as in Preparation Example A2-1, and as a result, had a volume average particle diameter Dv of 9 μm, a granularity distribution Dv/Dn of 1.68, and an average circularity of 0.77.

A crystal phase of the prepared α-TCP powder was identified in the same manner as in Preparation Example A2-1. As a result, the crystal phase thereof turned out to be α.

—Treatment for Imparting Organic Compound Having Phosphate Group or Carboxyl Group to Calcium Phosphate Powder—

The α-TCP powder (30 g), a 50% by mass phytic acid (manufactured by Wako Pure Chemical Industries, Ltd., having 6 phosphate groups) as an organic compound having phosphate group (0.2 g), ion-exchanged water (120 g), and zirconia beads having a diameter of 3 mm (540 g) were put into a 500 mL wide-mouth bottle, and subjected to wet milling by a ball mill for 2 hours. Then, the resultant was filtered and dried, and a resulting powder product was subjected to dry milling, to thereby obtain a layer stack formation powder material B1, which was an α-TCP powder having the phytic acid imparted on the surface thereof.

The imparting amount (abundance) of the phytic acid as the organic compound having phosphate group over the surface of the obtained layer stack formation powder material B1, which was an α-TCP powder, was measured with an elemental analyzer (ICPE-9000 manufactured by Shimadzu Corporation). As a result, the imparting amount was 5,000 ppm.

Preparation Example B2

Preparation of Layer Stack Formation Powder Material B2

Synthesis of Tricalcium Phosphate (β-TCP)

A 0.342 mol/dm$^3$ phosphoric acid aqueous solution was delivered at a speed of 6 mL/min into a 0.513 mol/dm$^3$ calcium hydroxide suspension liquid stirred with a commercially available paddle at 160 rpm, and their pH was stabilized to about 8.7 with ammonia. Then, the resultant was aged with an incubator of 37° C. for 72 hours, filtered, and then dried, to thereby obtain a powder product. Then, the powder product was burned under 800° C. conditions for 1 hour, and then subjected to ball mill pulverization with zirconia beads having a diameter of 3 mm. Here, ball mill pulverization was performed with BM-6 TYPE ROLLER BALL MILL manufactured by Glen Creston Ltd. When 30-minute pulverization was completed, the resultant was filtered through a 75 μm mesh, to thereby obtain minute particles. Then, the minute particles were burned at 1,100° C. for 5 hours, and then quenched, to thereby obtain a β-tricalcium phosphate (β-TCP) powder.

The obtained β-TCP powder was measured in the same manner as in Preparation Example A2-1, and as a result, had a volume average particle diameter Dv of 5 μm, a granularity distribution Dv/Dn of 1.45, and an average circularity of 0.78.

A crystal phase of the obtained calcium phosphate was identified in the same manner as in Preparation Example A2-1. As a result, the crystal phase thereof turned out to be β.

—Treatment for Imparting Organic Compound Having Phosphate Group or Carboxyl Group to Calcium Phosphate Powder—

The β-TCP powder (30 g), a 50% by mass phytic acid (manufactured by Wako Pure Chemical Industries, Ltd., having 6 phosphate groups) as an organic compound having phosphate group (0.2 g), ion-exchanged water (120 g), and zirconia beads having a diameter of 3 mm (540 g) were put into a 500 mL wide-mouth bottle, and subjected to wet milling by a ball mill for 2 hours. Then, the resultant was filtered and dried, and a resulting powder product was subjected to dry milling, to thereby obtain a layer stack formation powder material B2, which was a β-TCP powder having the phytic acid imparted on the surface thereof.

The imparting amount (abundance) of the phytic acid as the organic compound having phosphate group over the surface of the obtained layer stack formation powder material B2, which was a β-TCP powder, was measured in the same manner as in Preparation Example B1. As a result, the imparting amount was 5,000 ppm.

Preparation Example B3

Preparation of Layer Stack Formation Powder Material B3

Synthesis of Octacalcium Phosphate (OCP)

A 0.342 mol/dm$^3$ phosphoric acid aqueous solution was delivered at a speed of 6 mL/min into a 0.455 mol/dm$^3$ calcium hydroxide suspension liquid stirred with a commercially available paddle at 160 rpm, and their pH was stabilized to about 8.7 with ammonia. Then, the resultant was aged with an incubator of 37° C. for 72 hours, filtered, and then dried, to thereby obtain a powder product. Then, the powder product was burned under 800° C. conditions for 1 hour, and then subjected to ball mill pulverization with zirconia beads having a diameter of 3 mm. Here, ball mill pulverization was performed with BM-6 TYPE ROLLER BALL MILL manufactured by Glen Creston Ltd. When 30-minute pulverization was completed, the resultant was filtered through a 75 μm mesh, to thereby obtain minute particles. Then, the minute particles were burned at 1,100° C. for 5 hours, and then quenched, to thereby obtain an octacalcium phosphate (OCP) powder.

The obtained OCP powder was measured in the same manner as in Preparation Example A2-1, and as a result, had a volume average particle diameter Dv of 7 μm, a granularity distribution Dv/Dn of 1.73, and an average circularity of 0.78.

—Treatment for Imparting Organic Compound Having Phosphate Group or Carboxyl Group to Calcium Phosphate Powder—

The OCP powder (30 g), a 50% by mass phytic acid (manufactured by Wako Pure Chemical Industries, Ltd., having 6 phosphate groups) as an organic compound having phosphate group (0.2 g), ion-exchanged water (120 g), and zirconia beads having a diameter of 3 mm (540 g) were put into a 500 mL wide-mouth bottle, and subjected to wet milling by a ball mill for 2 hours. Then, the resultant was filtered and dried, and a resulting powder product was subjected to dry milling, to thereby obtain a layer stack formation powder material B3, which was an OCP powder having the phytic acid imparted on the surface thereof.

The imparting amount (abundance) of the phytic acid as the organic compound having phosphate group over the obtained layer stack formation powder material B3 was measured in the same manner as in Preparation Example B1. As a result, the imparting amount was 5,000 ppm.

Preparation Example B4

Preparation of Hardening Liquid B1

Water (60 parts by mass), a hardening agent, which is a citric acid (manufactured by Wako Pure Chemical Industries, Ltd.) (20 parts by mass), and a surfactant, which is TRITON X-100 (manufactured by Tokyo Chemical Industry Co., Ltd.) (0.5 parts by mass), were mixed and dispersed with a homomixer for 5 minutes, to thereby prepare a hardening liquid B1.

Example B1-1

A layer stack object B1-1 was formed in the manner described below, using the obtained layer stack formation powder material B1 and hardening liquid B1, and a shape printing pattern having a size of 70 mm in length and 12 mm in width.

(1) First, using such a publicly-known powder layer stack formation apparatus as shown in FIG. 1, the layer stack formation powder material B1 was delivered from the supply-side powder storage tank to the formation-side powder storage tank, to thereby form a thin layer of the layer stack formation powder material B1 having an average thickness of 100 μm over the support member.

(2) Next, using an inkjet printer (SG7100 manufactured by Ricoh Company, Ltd.), the hardening liquid B1 was delivered (discharged) onto the surface of the formed thin layer of the layer stack formation powder material B1 from a nozzle, to harden the layer stack formation powder material B1, to thereby harden the calcium phosphate.

(3) Next, the operations (1) and (2) were repeated up to a predetermined total average thickness of 3 mm, and hardened thin layers of the layer stack formation powder material B1 were stacked up sequentially, to thereby form a layer stack object B1-1. The obtained layer stack object B1-1 was air-blown to remove any excess of the layer stack formation powder material, and as a result, did not have a shape collapse. The obtained layer stack object B1-1 was excellent in strength and dimensional precision.

A hydroxyapatite (HAp) transformation rate, cytotoxicity, strength (hardness), and dimensional precision of the obtained layer stack object B1-1 were evaluated in the same manner as in Example A1-1. The results are shown in Table B2.

(4) The layer stack object B1-1 obtained in (3) was sintered in a sintering furnace under vacuum conditions at 1,300° C. The sintered product of the layer stack object B1-1 was a completely integrated calcium phosphate structure, and had no breakage or the like when slammed to a hard floor.

Example B2-1

A layer stack object B2-1 was formed in the same manner as in Example B1-1, except that the treatment for imparting an organic compound having phosphate group or carboxyl group to the calcium phosphate powder used in Example B1-1 was changed as follows.

The obtained layer stack object B2-1 was evaluated in the same manner as in Example B1-1. The results are shown in Table B2.

—Treatment for Imparting Organic Compound Having Phosphate Group or Carboxyl Group to Calcium Phosphate Powder—

The α-TCP powder (30 g), a 50% by mass phytic acid (manufactured by Wako Pure Chemical Industries, Ltd., having 6 phosphate groups) as an organic compound having phosphate group (0.05 g), ion-exchanged water (120 g), and zirconia beads having a diameter of 3 mm (540 g) were put into a 500 mL wide-mouth bottle, and subjected to wet milling by a ball mill for 2 hours. Then, the resultant was filtered and dried, and a resulting powder product was subjected to dry milling, to thereby obtain a layer stack formation powder material B4, which was an α-TCP powder having the phytic acid imparted on the surface thereof.

The imparting amount (abundance) of the phytic acid as the organic compound having phosphate group over the surface of the obtained layer stack formation powder material B4, which was an α-TCP powder, was measured in the same manner as in Preparation Example B1. As a result, the imparting amount was 1,000 ppm.

Example B3-1

A layer stack object B3-1 was formed in the same manner as in Example B1-1, except that the treatment for imparting an organic compound having phosphate group or carboxyl group to the calcium phosphate powder used in Example B1-1 was changed as follows.

The obtained layer stack object B3-1 was evaluated in the same manner as in Example B1-1. The results are shown in Table B2.

—Treatment for Imparting Organic Compound Having Phosphate Group or Carboxyl Group to Calcium Phosphate Powder—

The α-TCP powder (30 g), a 50% by mass phytic acid (manufactured by Wako Pure Chemical Industries, Ltd., having 6 phosphate groups) as an organic compound having phosphate group (0.5 g), ion-exchanged water (120 g), and zirconia beads having a diameter of 3 mm (540 g) were put into a 500 mL wide-mouth bottle, and subjected to wet milling by a ball mill for 2 hours. Then, the resultant was filtered and dried, and a resulting powder product was subjected to dry milling, to thereby obtain a layer stack formation powder material B5, which was an α-TCP powder having the phytic acid imparted on the surface thereof.

The imparting amount (abundance) of the phytic acid as the organic compound having phosphate group over the surface of the obtained layer stack formation powder material B5, which was an α-TCP powder, was measured in the same manner as in Preparation Example B1. As a result, the imparting amount was 10,000 ppm.

Example B4-1

A layer stack object B4-1 was formed in the same manner as in Example B1-1, except that the α-TCP powder used in Example B1-1 was changed to the layer stack formation powder material B2, which was obtained by imparting a phytic acid over the surface of the β-TCP powder prepared in Preparation Example B2.

The obtained layer stack object B4-1 was evaluated in the same manner as in Example B1-1. The results are shown in Table B2.

Example B5-1

A layer stack object B5-1 was formed in the same manner as in Example B1-1, except that the α-TCP powder used in Example B1-1 was changed to the layer stack formation powder material B3, which was obtained by imparting a phytic acid over the surface of the OCP powder prepared in Preparation Example B3.

The obtained layer stack object B5-1 was evaluated in the same manner as in Example B1-1. The results are shown in Table B2.

Example B6-1

A layer stack object B6-1 was formed in the same manner as in Example B1-1, except that the treatment for imparting an organic compound having phosphate group or carboxyl group to the calcium phosphate powder used in Example B1-1 was changed as follows.

The obtained layer stack object B6-1 was evaluated in the same manner as in Example B1-1. The results are shown in Table B2.

—Treatment for Imparting Organic Compound Having Phosphate Group or Carboxyl Group to Calcium Phosphate Powder—

The α-TCP powder (30 g), a citric acid (manufactured by Wako Pure Chemical Industries, Ltd., having 3 carboxyl groups) as an organic compound having carboxyl group (0.5 g), ion-exchanged water (120 g), and zirconia beads having a diameter of 3 mm (540 g) were put into a 500 mL wide-mouth bottle, and subjected to wet milling by a ball mill for 2 hours. Then, the resultant was filtered and dried, and a resulting powder product was subjected to dry milling, to thereby obtain a layer stack formation powder material B6, which was an α-TCP powder having the citric acid imparted on the surface thereof.

The imparting amount (abundance) of the citric acid as the organic compound having carboxyl group over the surface of the obtained layer stack formation powder material B6, which was an α-TCP powder, was measured according to LC-MS. As a result, the imparting amount was 6,000 ppm.

Example B7-1

A layer stack object B7-1 was formed in the same manner as in Example B1-1, except that the treatment for imparting an organic compound having phosphate group or carboxyl group to the calcium phosphate powder used in Example B1-1 was changed as follows.

The obtained layer stack object B7-1 was evaluated in the same manner as in Example B1-1. The results are shown in Table B2.

—Treatment for Imparting Organic Compound Having Phosphate Group or Carboxyl Group to Calcium Phosphate Powder—

The α-TCP powder (30 g), a 35% by mass etidronic acid (manufactured by Dojindo Laboratories, Co., Ltd., having 2 phosphate groups) as an organic compound having phosphate group (0.05 g), ion-exchanged water (120 g), and zirconia beads having a diameter of 3 mm (540 g) were put into a 500 mL wide-mouth bottle, and subjected to wet milling by a ball mill for 2 hours. Then, the resultant was filtered and dried, and a resulting powder product was subjected to dry milling, to thereby obtain a layer stack formation powder material B7, which was an α-TCP powder having the etidronic acid imparted on the surface thereof.

The imparting amount (abundance) of the etidronic acid as the organic compound having phosphate group over the surface of the obtained layer stack formation powder material B7, which was an α-TCP powder, was measured in the same manner as in Preparation Example B1. As a result, the imparting amount was 3,400 ppm.

Example B8-1

A layer stack object B8-1 was formed as described below according to electron beam irradiation (EBM) instead of the ink jetting used in Example B1-1. Electron beam irradiation (EBM) was performed with a homebuilt electron beam irradiator.

(1) First, using such a publicly-known powder layer stack formation apparatus as shown in FIG. 1, the layer stack formation powder material B1 was delivered from the supply-side powder storage tank to the formation-side powder storage tank, to thereby form a thin layer of the layer stack formation powder material B1 having an average thickness of 100 μm over the support member.

(2) Next, an electron beam was emitted to the surface of the formed thin layer of the layer stack formation powder material B1, to sinter the layer stack formation powder material B1, to thereby sinter the calcium phosphate.

(3) Next, the operations (1) and (2) were repeated up to a predetermined total average thickness of 3 mm, and thin layers of the layer stack formation powder material B1 were stacked up sequentially, to thereby form a layer stack object B8-1.

The obtained layer stack object B8-1 was air-blown to remove any excess of the layer stack formation powder material B1, and as a result, did not have a shape collapse. The obtained sintered product of the layer stack object B8-1 was excellent in strength and dimensional precision.

The obtained layer stack object B8-1 was evaluated in the same manner as in Example B1-1. The results are shown in Table B2.

Example B9-1

A layer stack object B9-1 was formed as described below according to laser irradiation instead of the ink jetting used in Example B1-1. The laser used was a $CO_2$ laser (LP-400 manufactured by SUNX Co., Ltd.).

(1) First, using such a publicly-known powder layer stack formation apparatus as shown in FIG. 1, the layer stack formation powder material B1 was delivered from the supply-side powder storage tank to the formation-side powder storage tank, to thereby form a thin layer of the layer stack formation powder material B1 having an average thickness of 100 μm over the support member.

(2) The $CO_2$ laser was emitted to the surface of the formed thin layer of the layer stack formation powder material B1, to sinter the layer stack formation powder material B1, to thereby sinter the calcium phosphate.

(3) Next, the operations (1) and (2) were repeated up to a predetermined total average thickness of 3 mm, and thin layers of the layer stack formation powder material B1 were stacked up sequentially, to thereby form a layer stack object B9-1.

The obtained layer stack object B9-1 was air-blown to remove any excess of the layer stack formation powder material, and as a result, did not have a shape collapse. The obtained sintered product of the layer stack object B9-1 was excellent in strength and dimensional precision.

The obtained layer stack object B9-1 was evaluated in the same manner as in Example B1-1. The results are shown in Table B2.

Comparative Example B1-1

A layer stack object B10-1 was formed in the same manner as in Example B1-1, except that the treatment for imparting an organic compound having phosphate group or carboxyl group to the calcium phosphate powder used in Example B1-1 was changed as follows.

The obtained layer stack object B10-1 was evaluated in the same manner as in Example B1-1. The results are shown in Table B2.

—Treatment for Imparting Organic Compound Having Phosphate Group or Carboxyl Group to Calcium Phosphate Powder—

The α-TCP powder (30 g), a 50% by mass phytic acid (manufactured by Wako Pure Chemical Industries, Ltd., having 6 phosphate groups) as an organic compound having phosphate group (0.04 g), ion-exchanged water (120 g), and zirconia beads having a diameter of 3 mm (540 g) were put into a 500 mL wide-mouth bottle, and subjected to wet milling by a ball mill for 2 hours. Then, the resultant was filtered and dried, and a resulting powder product was subjected to dry milling, to thereby obtain a layer stack formation powder material B8, which was an α-TCP powder having the phytic acid imparted on the surface thereof.

The imparting amount (abundance) of the phytic acid as the organic compound having phosphate group over the surface of the obtained layer stack formation powder material B8, which was an α-TCP powder, was measured in the same manner as in Preparation Example B1. As a result, the imparting amount was 800 ppm.

Comparative Example B2-1

A layer stack object B11-1 was formed in the same manner as in Example B1-1, except that the treatment for imparting an organic compound having phosphate group or carboxyl group to the calcium phosphate powder used in Example B1-1 was changed as follows.

The obtained layer stack object B11-1 was evaluated in the same manner as in Example B1-1. The results are shown in Table B2.

—Treatment for Imparting Organic Compound Having Phosphate Group or Carboxyl Group to Calcium Phosphate Powder—

The α-TCP powder (30 g), a 50% by mass phytic acid (manufactured by Wako Pure Chemical Industries, Ltd., having 6 phosphate groups) as an organic compound having phosphate group (0.6 g), ion-exchanged water (120 g), and zirconia beads having a diameter of 3 mm (540 g) were put into a 500 mL wide-mouth bottle, and subjected to wet milling by a ball mill for 2 hours. Then, the resultant was filtered and dried, and a resulting powder product was subjected to dry milling, to thereby obtain a layer stack formation powder material B9, which was an α-TCP powder having the phytic acid imparted on the surface thereof.

The imparting amount (abundance) of the phytic acid as the organic compound having phosphate group over the surface of the obtained layer stack formation powder material B9, which was an α-TCP powder, was measured in the same manner as in Preparation Example B1. As a result, the imparting amount was 11,000 ppm.

Comparative Example B3-1

A layer stack object B12-1 was formed in the same manner as in Example B1-1, except that the treatment for imparting an organic compound having phosphate group or carboxyl group to the calcium phosphate powder used in Example B1-1 was changed as follows. The obtained layer stack object B12-1 was evaluated in the same manner as in Example B1-1. The results are shown in Table B2.

—Treatment for Imparting Organic Compound Having Phosphate Group or Carboxyl Group to Calcium Phosphate Powder—

The α-TCP powder (30 g), a polyphosphoric acid (manufactured by Tokyo Chemical Industry Co., Ltd., having 15 phosphate groups, and a weight average molecular weight of 1,200) as an organic compound having phosphate group (0.4 g), ion-exchanged water (120 g), and zirconia beads having a diameter of 3 mm (540 g) were put into a 500 mL wide-mouth bottle, and subjected to wet milling by a ball mill for 2 hours. Then, the resultant was filtered and dried, and a resulting powder product was subjected to dry milling, to thereby obtain a layer stack formation powder material B10, which was an α-TCP powder having the polyphosphoric acid imparted on the surface thereof.

The imparting amount (abundance) of the polyphosphoric acid as the organic compound having phosphate group over the surface of the obtained layer stack formation powder material B10, which was an α-TCP powder, was measured in the same manner as in Preparation Example B1. As a result, the imparting amount was 100 ppm.

Comparative Example B4-1

A layer stack object B13-1 was formed in the same manner as in Example B1-1, except that the treatment for imparting an organic compound having phosphate group or carboxyl group to the calcium phosphate powder used in Example B1-1 was changed as follows.

The obtained layer stack object B13-1 was evaluated in the same manner as in Example B1-1. The results are shown in Table B2.

—Treatment for Imparting Organic Compound Having Phosphate Group or Carboxyl Group to Calcium Phosphate Powder—

The α-TCP powder (30 g), inositol trisphosphate (manufactured by Dojindo Laboratories, Co., Ltd., having 3 phosphate groups) as an organic compound having phosphate group (0.4 g), ion-exchanged water (120 g), and zirconia beads having a diameter of 3 mm (540 g) were put into a 500 mL wide-mouth bottle, and subjected to wet milling by a ball mill for 2 hours. Then, the resultant was filtered and dried, and a resulting powder product was subjected to dry milling, to thereby obtain a layer stack formation powder material B11, which was an α-TCP powder having the inositol trisphosphate imparted on the surface thereof.

The imparting amount (abundance) of the inositol trisphosphate as the organic compound having phosphate group over the surface of the obtained layer stack formation powder material B11, which was an α-TCP powder, was measured in the same manner as in Preparation Example B1. As a result, the imparting amount was 300 ppm.

Comparative Example B5-1

A layer stack object B14-1 was formed in the same manner as in Example B1-1, except that the treatment for imparting an organic compound having phosphate group or carboxyl group to the calcium phosphate powder used in Example B1-1 was changed as follows.

The obtained layer stack object B14-1 was evaluated in the same manner as in Example B1-1. The results are shown in Table B2.

—Treatment for Imparting Organic Compound Having Phosphate Group or Carboxyl Group to Calcium Phosphate Powder—

The α-TCP powder (30 g), a citric acid (manufactured by Wako Pure Chemical Industries, Ltd., having 3 carboxyl groups) as an organic compound having carboxyl group (0.04 g), ion-exchanged water (120 g), and zirconia beads having a diameter of 3 mm (540 g) were put into a 500 mL wide-mouth bottle, and subjected to wet milling by a ball mill for 2 hours. Then, the resultant was filtered and dried, and a resulting powder product was subjected to dry milling, to thereby obtain a layer stack formation powder material B12, which was an α-TCP powder having the citric acid imparted on the surface thereof.

The imparting amount (abundance) of the citric acid as the organic compound having carboxyl group over the surface of the obtained layer stack formation powder material B12, which was an α-TCP powder, was measured in the same manner as in Example B6-1. As a result, the imparting amount was 400 ppm.

Comparative Example B6-1

A layer stack object B15-1 was formed in the same manner as in Example B1-1, except that the treatment for imparting an organic compound having phosphate group or carboxyl group to the calcium phosphate powder used in Example B1-1 was not performed, and that the α-TCP powder prepared in Preparation Example B1 was used as a layer stack formation powder material B13.

The obtained layer stack object B15-1 was evaluated in the same manner as in Example B1-1. The results are shown in Table B2.

Comparative Example B7-1

A layer stack object B16-1 was formed in the same manner as in Example B8-1, except that the layer stack formation powder material B8 was used instead of the layer stack formation powder material B1 of Example B8-1.

The obtained layer stack object B16-1 was evaluated in the same manner as in Example B1-1. The results are shown in Table B2.

Comparative Example B8-1

A layer stack object B17-1 was formed in the same manner as in Example B8-1, except that the layer stack formation powder material B9 was used instead of the layer stack formation powder material B1 of Example B8-1.

The obtained layer stack object B17-1 was evaluated in the same manner as in Example B1-1. The results are shown in Table B2.

Comparative Example B9-1

A layer stack object B18-1 was formed in the same manner as in Example B9-1, except that the layer stack formation powder material B8 was used instead of the layer stack formation powder material B1 of Example B9-1.

The obtained layer stack object B18-1 was evaluated in the same manner as in Example B1-1. The results are shown in Table B2.

Comparative Example B10-1

A layer stack object B19-1 was formed in the same manner as in Example B9-1, except that the layer stack formation powder material B9 was used instead of the layer stack formation powder material B1 of Example B9-1.

The obtained layer stack object B19-1 was evaluated in the same manner as in Example B1-1. The results are shown in Table B2.

TABLE B1

| | | | Layer stack formation powder material | | | |
| | | | | Organic compound having phosphate group or carboxyl group | | |
| | No. | Kind of calcium phosphate powder | Kind | Monomer/ polymer | Number of phosphate or carboxyl groups | Imparting amount to calcium phosphate powder surface (ppm) |
|---|---|---|---|---|---|---|
| Ex. B1-1 | 1 | α-TCP | Phytic acid | Monomer | 6 | 5,000 |
| Ex. B2-1 | 4 | α-TCP | Phytic acid | Monomer | 6 | 1,000 |
| Ex. B3-1 | 5 | α-TCP | Phytic acid | Monomer | 6 | 10,000 |
| Ex. B4-1 | 2 | β-TCP | Phytic acid | Monomer | 6 | 5,000 |
| Ex. B5-1 | 3 | OCP | Phytic acid | Monomer | 6 | 5,000 |
| Ex. B6-1 | 6 | α-TCP | Citric acid | Monomer | 3 | 6,000 |
| Ex. B7-1 | 7 | α-TCP | Etidronic acid | Monomer | 2 | 3,400 |
| Ex. B8-1 | 1 | α-TCP | Phytic acid | Monomer | 6 | 5,000 |
| Ex. B9-1 | 1 | α-TCP | Phytic acid | Monomer | 6 | 5,000 |
| Comp. Ex. B1-1 | 8 | α-TCP | Phytic acid | Monomer | 6 | 800 |
| Comp. Ex. B2-1 | 9 | α-TCP | Phytic acid | Monomer | 6 | 11,000 |
| Comp. Ex. B3-1 | 10 | α-TCP | Polyphosphoric acid | Polymer | 15 | 100 |
| Comp. Ex. B4-1 | 11 | α-TCP | Inositol trisphosphate | Monomer | 3 | 300 |
| Comp. Ex. B5-1 | 12 | α-TCP | Citric acid | Monomer | 3 | 400 |
| Comp. Ex. B6-1 | 13 | α-TCP | Absent | — | — | — |
| Comp. Ex. B7-1 | 8 | α-TCP | Phytic acid | Monomer | 6 | 800 |
| Comp. Ex. B8-1 | 9 | α-TCP | Phytic acid | Monomer | 6 | 11,000 |
| Comp. Ex. B9-1 | 8 | α-TCP | Phytic acid | Monomer | 6 | 800 |
| Comp. Ex. B10-1 | 9 | α-TCP | Phytic acid | Monomer | 6 | 11,000 |

TABLE B2

| | Hardening liquid | Hardening/sintering method | HAp transformation rate (%) | Cytotoxicity | Strength | Dimensional precision |
|---|---|---|---|---|---|---|
| Ex. B1-1 | Hardening liquid 1 | Inkjet | 0.3 | Absent | A | B |
| Ex. B2-1 | Hardening liquid 1 | Inkjet | 0.9 | Absent | B | B |
| Ex. B3-1 | Hardening liquid 1 | Inkjet | 0.1 | Absent | A | B |
| Ex. B4-1 | Hardening liquid 1 | Inkjet | 0.1 | Absent | A | B |
| Ex. B5-1 | Hardening liquid 1 | Inkjet | 0.4 | Absent | A | B |
| Ex. B6-1 | Hardening liquid 1 | Inkjet | 0.7 | Absent | A | B |
| Ex. B7-1 | Hardening liquid 1 | Inkjet | 0.2 | Absent | A | B |
| Ex. B8-1 | Absent | Electron beam irradiation | 0.3 | Absent | A | B |
| Ex. B9-1 | Absent | $CO_2$ laser | 0.3 | Absent | A | B |
| Comp. Ex. B1-1 | Hardening liquid 1 | Inkjet | 1.1 | Absent | D | B |
| Comp. Ex. B2-1 | Hardening liquid 1 | Inkjet | 0.1 | Present | A | B |
| Comp. Ex. B3-1 | Hardening liquid 1 | Inkjet | 8.2 | Absent | D | B |
| Comp. Ex. B4-1 | Hardening liquid 1 | Inkjet | 4.9 | Absent | D | B |
| Comp. Ex. B5-1 | Hardening liquid 1 | Inkjet | 1.7 | Absent | D | B |
| Comp. Ex. B6-1 | Hardening liquid 1 | Inkjet | 16.3 | Absent | D | B |
| Comp. Ex. B7-1 | Absent | Electron beam irradiation | 1.2 | Absent | A | B |
| Comp. Ex. B8-1 | Absent | Electron beam irradiation | 0.1 | Present | A | B |
| Comp. Ex. B9-1 | Absent | $CO_2$ laser | 1.1 | Absent | A | B |
| Comp. Ex. B10-1 | Absent | $CO_2$ laser | 0.1 | Present | A | B |

From the results of Table B1 and Table B2, Comparative Example B2-1, Comparative Example B8-1, and Comparative Example B10-1 achieved favorable results in terms of strength and dimensional precision, but had cytotoxicity because of an excessively high phytic acid imparting amount, and had a risk of expressing cytotoxicity when transplanted into a living body.

Comparative Example B1-1, Comparative Examples B3-1 to B7-1, and Comparative Example B9-1 had a HAp transformation rate of higher than 1%, and when transplanted into a living body, would have a trouble of transforming to hydroxyapatite (HAp) and remaining in the living body.

Preparation Example B5

Preparation of Layer Stack Formation Powder Material B101

Preparation of Powder Made of Organic Compound Having Phosphate Group or Carboxyl Group A 50% by mass phytic acid (manufactured by Wako Pure Chemical Industries, Ltd., having 6 phosphate groups) was freeze-dried at −40° C. at a reduced pressure of 0.1 Torr, and pulverized under cooling conditions. After this, the freeze-pulverized phytic acid was put and shaken over a sieve having a mesh of 75 μm, and particles that passed through the sieve were used as a powder made of an organic compound having phosphate group.

—Mixing of Calcium Phosphate Powder with Powder Made of Organic Compound Having Phosphate Group or Carboxyl Group—

The powder made of an organic compound having phosphate group was mixed with the α-TCP powder (100 g) prepared in Preparation Example B1, such that the former would be in an amount of 15% by mass relative to the latter, and they were Oster-blended under cooling conditions, to thereby obtain a layer stack formation powder material B101.

Preparation Example B6

Preparation of Hardening Liquid B2

Water (100 parts by mass), and a surfactant, which was TRITON X-100 (manufactured by Tokyo Chemical Industry Co., Ltd.) (0.5 parts by mass) were mixed and dispersed with a homomixer for 5 minutes, to thereby prepare a hardening liquid B2.

Example B1-2

A layer stack object B1-2 was formed in the manner described below, using the obtained layer stack formation powder material B101 and hardening liquid B2, and a shape printing pattern having a size of 70 mm in length and 12 mm in width.

(1) First, using such a publicly-known powder layer stack formation apparatus as shown in FIG. 1, the layer stack formation powder material B101 was delivered from the supply-side powder storage tank to the formation-side powder storage tank, to thereby form a thin layer of the layer stack formation powder material B101 having an average thickness of 100 µm over the support member.

(2) Next, using an inkjet printer (SG7100 manufactured by Ricoh Company, Ltd.), the hardening liquid B2 was delivered (discharged) onto the surface of the formed thin layer of the layer stack formation powder material B101 from a nozzle, to harden the layer stack formation powder material B101, to thereby harden the calcium phosphate.

(3) Next, the operations (1) and (2) were repeated up to a predetermined total average thickness of 3 mm, and hardened thin layers of the layer stack formation powder material B101 were stacked up sequentially, to thereby form a layer stack object B1-2. The obtained layer stack object B1-2 was air-blown to remove any excess of the layer stack formation powder material, and as a result, did not have a shape collapse. The obtained layer stack object B1-2 was excellent in strength and dimensional precision.

A hydroxyapatite transformation rate (HAp transformation rate), cytotoxicity, strength (hardness), and dimensional precision of the obtained layer stack object B1-2 were evaluated in the same manner as in Example B1-1. The results are shown in Table B4.

(4) The layer stack object B1-2 obtained in (3) was sintered in a sintering furnace under vacuum conditions at 1,300° C. The sintered product of the layer stack object B1-2 was a completely integrated calcium phosphate structure, and had no breakage or the like when slammed to a hard floor.

Example B2-2

A layer stack object B2-2 was formed in the same manner as in Example B1-2, except that the layer stack formation powder material B101 used in Example B1-2 was changed to a layer stack formation powder material B102 prepared as follows.

The obtained layer stack object B2-2 was evaluated in the same manner as in Example B1-1. The results are shown in Table B4.
<Preparation of Layer Stack Formation Powder Material B102>
—Preparation of Powder Made of Organic Compound Having Phosphate Group or Carboxyl Group—

An etidronic acid (manufactured by Dojindo Laboratories, Co., Ltd., having 2 phosphate groups) was freeze-dried at −40° C. at a reduced pressure of 0.1 Torr, and pulverized under cooling conditions. After this, the freeze-pulverized etidronic acid was put and shaken over a sieve having a mesh of 75 µm, and particles that passed through the sieve were used as a powder made of an organic compound having phosphate group.
—Mixing of Calcium Phosphate Powder with Powder made of Organic Compound Having Phosphate Group or Carboxyl Group—

The powder made of an organic compound having phosphate group was mixed with the α-TCP powder (100 g) prepared in Preparation Example B1, such that the former would be in an amount of 15% by mass relative to the latter, and they were Oster-blended under cooling conditions, to thereby obtain a layer stack formation powder material B102.

Example B3-2

A layer stack object B3-2 was formed in the same manner as in Example B1-2, except that the layer stack formation powder material B101 used in Example B1-2 was changed to a layer stack formation powder material B103 prepared as follows.

The obtained layer stack object B3-2 was evaluated in the same manner as in Example B1-1. The results are shown in Table B4.
—Preparation of Powder Made of Organic Compound Having Phosphate Group or Carboxyl Group—
<Preparation of Layer Stack Formation Powder Material B103>

A citric acid (manufactured by Wako Pure Chemical Industries, Ltd., having 3 carboxyl groups) was freeze-dried at −40° C. at a reduced pressure of 0.1 Torr, and pulverized under cooling conditions. After this, the freeze-pulverized citric acid was put and shaken over a sieve having a mesh of 75 µm, and particles that passed through the sieve were used as a powder made of an organic compound having carboxyl group.
—Mixing of Calcium Phosphate Powder with Powder made of Organic Compound Having Phosphate Group or Carboxyl Group—

The powder made of an organic compound having carboxyl group was mixed with the α-TCP powder (100 g) prepared in Preparation Example B1, such that the former would be in an amount of 15% by mass relative to the latter, and they were Oster-blended under cooling conditions, to thereby obtain a layer stack formation powder material B103.

Example B4-2

A layer stack object B4-2 was formed in the same manner as in Example B1-2, except that the layer stack formation powder material B101 used in Example B1-2 was changed to a layer stack formation powder material B104 prepared as follows.

The obtained layer stack object B4-2 was evaluated in the same manner as in Example B1-1. The results are shown in Table B4.
<Preparation of Layer Stack Formation Powder Material B104>
—Preparation of Powder Made of Organic Compound Having Phosphate Group or Carboxyl Group—

A 50% by mass phytic acid (manufactured by Wako Pure Chemical Industries, Ltd., having 6 phosphate groups) was freeze-dried at −40° C. at a reduced pressure of 0.1 Torr, and pulverized under cooling conditions. After this, the freeze-pulverized phytic acid was put and shaken over a sieve having a mesh of 75 µm, and particles that passed through the sieve were used as a powder made of an organic compound having phosphate group.
—Mixing of Calcium Phosphate Powder with Powder made of Organic Compound Having Phosphate Group or Carboxyl Group—

The powder made of an organic compound having phosphate group was mixed with the β-TCP powder (100 g) prepared in Preparation Example B2, such that the former would be in an amount of 15% by mass relative to the latter, and they were Oster-blended under cooling conditions, to thereby obtain a layer stack formation powder material B104.

Example B5-2

A layer stack object B5-2 was formed in the same manner as in Example B1-2, except that the layer stack formation powder material B101 used in Example B1-2 was changed to a layer stack formation powder material B105 prepared as follows.

The obtained layer stack object B5-2 was evaluated in the same manner as in Example B1-1. The results are shown in Table B4.

<Preparation of Layer Stack Formation Powder Material B105>
—Preparation of Powder Made of Organic Compound Having Phosphate Group or Carboxyl Group—

A 50% by mass phytic acid (manufactured by Wako Pure Chemical Industries, Ltd., having 6 phosphate groups) was freeze-dried at −40° C. at a reduced pressure of 0.1 Torr, and pulverized under cooling conditions. After this, the freeze-pulverized phytic acid was put and shaken over a sieve having a mesh of 75 μm, and particles that passed through the sieve were used as a powder made of an organic compound having phosphate group.
—Mixing of Calcium Phosphate Powder with Powder made of Organic Compound Having Phosphate Group or Carboxyl Group—

The powder made of an organic compound having phosphate group was mixed with the OCP powder (100 g) prepared in Preparation Example B3, such that the former would be in an amount of 15% by mass relative to the latter, and they were Oster-blended under cooling conditions, to thereby obtain a layer stack formation powder material B105.

Example B6-2

A layer stack object B6-2 was formed in the same manner as in Example B1-2, except that the layer stack formation powder material B101 used in Example B1-2 was changed to a layer stack formation powder material B106 prepared as follows.

The obtained layer stack object B6-2 was evaluated in the same manner as in Example B1-1. The results are shown in Table B4.

<Preparation of Layer Stack Formation Powder Material B106>
—Preparation of Powder Made of Organic Compound Having Phosphate Group or Carboxyl Group—

A 50% by mass phytic acid (manufactured by Wako Pure Chemical Industries, Ltd., having 6 phosphate groups) was freeze-dried at −40° C. at a reduced pressure of 0.1 Torr, and pulverized under cooling conditions. After this, the freeze-pulverized phytic acid was put and shaken over a sieve having a mesh of 75 μm, and particles that passed through the sieve were used as a powder made of an organic compound having phosphate group.
—Mixing of Calcium Phosphate Powder with Powder made of Organic Compound Having Phosphate Group or Carboxyl Group—

The powder made of an organic compound having phosphate group was mixed with the α-TCP powder (100 g) prepared in Preparation Example B1, such that the former would be in an amount of 10% by mass relative to the latter, and they were Oster-blended under cooling conditions, to thereby obtain a layer stack formation powder material B106.

Example B7-2

A layer stack object B7-2 was formed in the same manner as in Example B1-2, except that the layer stack formation powder material B101 used in Example B1-2 was changed to a layer stack formation powder material B107 prepared as follows.

The obtained layer stack object B7-2 was evaluated in the same manner as in Example B1-1. The results are shown in Table B4.

<Preparation of Layer Stack Formation Powder Material B107>
—Preparation of Powder Made of Organic Compound Having Phosphate Group or Carboxyl Group—

A 50% by mass phytic acid (manufactured by Wako Pure Chemical Industries, Ltd., having 6 phosphate groups) was freeze-dried at −40° C. at a reduced pressure of 0.1 Torr, and pulverized under cooling conditions. After this, the freeze-pulverized phytic acid was put and shaken over a sieve having a mesh of 75 μm, and particles that passed through the sieve were used as a powder made of an organic compound having phosphate group.
—Mixing of Calcium Phosphate Powder with Powder made of Organic Compound Having Phosphate Group or Carboxyl Group—

The powder made of an organic compound having phosphate group was mixed with the α-TCP powder (100 g) prepared in Preparation Example B1, such that the former would be in an amount of 50% by mass relative to the latter, and they were Oster-blended under cooling conditions, to thereby obtain a layer stack formation powder material B107.

Example B8-2

A layer stack object B8-2 was formed as described below according to laser irradiation instead of the ink jetting used in Example B1-2. The laser used was a $CO_2$ laser (LP-400 manufactured by SUNX Co., Ltd.).

(1) First, using such a publicly-known powder layer stack formation apparatus as shown in FIG. 1, the layer stack formation powder material B101 was delivered from the supply-side powder storage tank to the formation-side powder storage tank, to thereby form a thin layer of the layer stack formation powder material B101 having an average thickness of 100 μm over the support member.

(2) Next, the $CO_2$ laser was emitted to the surface of the formed thin layer of the layer stack formation powder material B101, to sinter the layer stack formation powder material B101, to thereby sinter the calcium phosphate.

(3) Next, the operations (1) and (2) were repeated up to a predetermined total average thickness of 3 mm, and thin layers of the layer stack formation powder material B101 were stacked up sequentially, to thereby form a layer stack object B8-2.

The obtained layer stack object B8-2 was air-blown to remove any excess of the layer stack formation powder material, and as a result, did not have a shape collapse. The obtained sintered product of the layer stack object B8-2 was excellent in strength and dimensional precision.

The obtained layer stack object B8-2 was evaluated in the same manner as in Example B1-1. The results are shown in Table B4.

Example B9-2

A layer stack object B9-2 was formed as described below according to electron beam irradiation (EBM) instead of the ink jetting used in Example B1-2. Electron beam irradiation (EBM) was performed with a homebuilt electron beam irradiator.

(1) First, using such a publicly-known powder layer stack formation apparatus as shown in FIG. 1, the layer stack formation powder material B101 was delivered from the supply-side powder storage tank to the formation-side powder storage tank, to thereby form a thin layer of the layer stack formation powder material B101 having an average thickness of 100 μm over the support member.

(2) Next, an electron beam was emitted to the surface of the formed thin layer of the layer stack formation powder material B101, to sinter the layer stack formation powder material B101, to thereby sinter the calcium phosphate.

(3) Next, the operations (1) and (2) were repeated up to a predetermined total average thickness of 3 mm, and thin layers of the layer stack formation powder material B101 were stacked up sequentially, to thereby form a layer stack object B9-2.

The obtained layer stack object B9-2 was air-blown to remove any excess of the layer stack formation powder material, and as a result, did not have a shape collapse. The obtained sintered product of the layer stack object B9-2 was excellent in strength and dimensional precision.

The obtained layer stack object B9-2 was evaluated in the same manner as in Example B1-1. The results are shown in Table B4.

Comparative Example B1-2

A layer stack object B10-2 was formed in the same manner as in Example B1-2, except that the layer stack formation powder material B101 used in Example B1-2 was changed to a layer stack formation powder material B108 prepared as follows.

The obtained layer stack object B10-2 was evaluated in the same manner as in Example B1-1. The results are shown in Table B4.

<Preparation of Layer Stack Formation Powder Material B108>

—Preparation of Powder Made of Organic Compound—

Inositol (manufactured by Shikishima Starch Mfg. Co., Ltd., having 0 phosphate group or carboxyl group) was filtered through a sieve having a mesh of 75 μM, and particles that passed through the sieve were used as a powder made of an organic compound.

—Mixing of Calcium Phosphate Powder with Powder made of Organic Compound—

The powder made of an organic compound was mixed with the α-TCP powder (100 g) prepared in Preparation Example B1, such that the former would be in an amount of 15% by mass relative to the latter, and they were Oster-blended under cooling conditions, to thereby obtain a layer stack formation powder material B108.

Comparative Example B2-2

A layer stack object B11-2 was formed in the same manner as in Example B1-2, except that the layer stack formation powder material B101 used in Example B1-2 was changed to a layer stack formation powder material B109 prepared as follows.

The obtained layer stack object B11-2 was evaluated in the same manner as in Example B1-1. The results are shown in Table B4.

<Preparation of Layer Stack Formation Powder Material B109>

—Preparation of Powder Made of Organic Compound Having Phosphate Group or Carboxyl Group—

A 50% by mass phytic acid (manufactured by Wako Pure Chemical Industries, Ltd., having 6 phosphate groups) was freeze-dried at −40° C. at a reduced pressure of 0.1 Torr, and pulverized under cooling conditions. After this, the freeze-pulverized phytic acid was put and shaken over a sieve having a mesh of 75 μm, and particles that passed through the sieve were used as a powder made of an organic compound having phosphate group.

—Mixing of Calcium Phosphate Powder with Powder made of Organic Compound Having Phosphate Group or Carboxyl Group—

The powder made of an organic compound having phosphate group was mixed with the α-TCP powder (100 g) prepared in Preparation Example B1, such that the former would be in an amount of 9% by mass relative to the latter, and they were Oster-blended under cooling conditions, to thereby obtain a layer stack formation powder material B109.

Comparative Example B3-2

A layer stack object B12-2 was formed in the same manner as in Example B1-2, except that the layer stack formation powder material B101 used in Example B1-2 was changed to a layer stack formation powder material B110 prepared as follows.

The obtained layer stack object B12-2 was evaluated in the same manner as in Example B1-1. The results are shown in Table B4.

<Preparation of Layer Stack Formation Powder Material B110>

—Preparation of Powder Made of Organic Compound Having Phosphate Group or Carboxyl Group—

A 50% by mass phytic acid (manufactured by Wako Pure Chemical Industries, Ltd., having 6 phosphate groups) was freeze-dried at −40° C. at a reduced pressure of 0.1 Torr, and pulverized under cooling conditions. After this, the freeze-pulverized phytic acid was put and shaken over a sieve having a mesh of 75 μm, and particles that passed through the sieve were used as a powder made of an organic compound having phosphate group.

—Mixing of Calcium Phosphate Powder with Powder made of Organic Compound Having Phosphate Group or Carboxyl Group—

The powder made of an organic compound having phosphate group was mixed with the α-TCP powder (100 g) prepared in Preparation Example B1, such that the former would be in an amount of 51% by mass relative to the latter, and they were Oster-blended under cooling conditions, to thereby obtain a layer stack formation powder material B110.

Comparative Example B4-2

A layer stack object B13-2 was formed in the same manner as in Example B1-2, except that the layer stack formation powder material B101 used in Example B1-2 was changed to a layer stack formation powder material B111 prepared as follows.

The obtained layer stack object B13-2 was evaluated in the same manner as in Example B1-1. The results are shown in Table B4.

<Preparation of Layer Stack Formation Powder Material B111>

—Preparation of Powder Made of Organic Compound Having Phosphate Group or Carboxyl Group—

A freeze-dried product of an acetic acid (manufactured by Asuzac Foods Co., Ltd., having 1 carboxyl group) was filtered through a sieve having a mesh of 75 μm, and particles that passed through the sieve were used as a powder made of an organic compound having carboxyl group.

—Mixing of Calcium Phosphate Powder with Powder made of Organic Compound Having Phosphate Group or Carboxyl Group—

The powder made of an organic compound having carboxyl group was mixed with the α-TCP powder (100 g) prepared in Preparation Example B1, such that the former would be in an amount of 15% by mass relative to the latter, and they were Oster-blended under cooling conditions, to thereby obtain a layer stack formation powder material B111.

Comparative Example B5-2

A layer stack object B14-2 was formed in the same manner as in Example B1-2, except that unlike in Example B1-2, a powder made of an organic compound having phosphate group or carboxyl group was not used, i.e., the α-TCP powder of Preparation Example B1 was used as a layer stack formation powder material B112.

The obtained layer stack object B14-2 was evaluated in the same manner as in Example B1-1. The results are shown in Table B4.

TABLE B3

| | | | Layer stack formation powder material | | | |
| --- | --- | --- | --- | --- | --- | --- |
| | | | | Powder made of organic compound having phosphate group or carboxyl group | | |
| | No. | Kind of calcium phosphate powder | Kind | Monomer/ polymer | Number of phosphate or carboxyl groups | Mixing amount (% by mass) |
| Ex. B1-2 | 101 | α-TCP | Phytic acid | Monomer | 6 | 15 |
| Ex. B2-2 | 102 | α-TCP | Etidronic acid | Monomer | 2 | 15 |
| Ex. B3-2 | 103 | α-TCP | Citric acid | Monomer | 3 | 15 |
| Ex. B4-2 | 104 | β-TCP | Phytic acid | Monomer | 6 | 15 |
| Ex. B5-2 | 105 | OCP | Phytic acid | Monomer | 6 | 15 |
| Ex. B6-2 | 106 | α-TCP | Phytic acid | Monomer | 6 | 10 |
| Ex. B7-2 | 107 | α-TCP | Phytic acid | Monomer | 6 | 50 |
| Ex. B8-2 | 101 | α-TCP | Phytic acid | Monomer | 6 | 15 |
| Ex. B9-2 | 101 | α-TCP | Phytic acid | Monomer | 6 | 15 |
| Comp. Ex. B1-2 | 108 | α-TCP | Inositol | Monomer | 0 | 15 |
| Comp. Ex. B2-2 | 109 | α-TCP | Phytic acid | Monomer | 6 | 9 |
| Comp. Ex. B3-2 | 110 | α-TCP | Phytic acid | Monomer | 6 | 51 |
| Comp. Ex. B4-2 | 111 | α-TCP | Acetic acid | Monomer | 1 | 15 |
| Comp. Ex. B5-2 | 112 | α-TCP | Absent | — | — | — |

TABLE B4

| | Hardening liquid | Hardening/ sintering method | HAp transformation rate (%) | Cytotoxicity | Strength | Dimensional precision |
| --- | --- | --- | --- | --- | --- | --- |
| Ex. B1-2 | Hardening liquid 2 | Inkjet | 0.3 | Absent | A | A |
| Ex. B2-2 | Hardening liquid 2 | Inkjet | 0.3 | Absent | A | A |
| Ex. B3-2 | Hardening liquid 2 | Inkjet | 0.9 | Absent | A | A |
| Ex. B4-2 | Hardening liquid 2 | Inkjet | 0.3 | Absent | B | B |
| Ex. B5-2 | Hardening liquid 2 | Inkjet | 0.4 | Absent | B | B |
| Ex. B6-2 | Hardening liquid 2 | Inkjet | 0.9 | Absent | B | A |
| Ex. B7-2 | Hardening liquid 2 | Inkjet | 0.1 | Absent | B | B |
| Ex. B8-2 | Absent | CO$_2$ laser | 0.8 | Absent | B | B |
| Ex. B9-2 | Absent | Electron beam irradiation | 0.8 | Absent | B | B |

TABLE B4-continued

| | Hardening liquid | Hardening/ sintering method | HAp transformation rate (%) | Cytotoxicity | Strength | Dimensional precision |
|---|---|---|---|---|---|---|
| Comp. Ex. B1-2 | Hardening liquid 2 | Inkjet | 18.9 | Absent | D | D |
| Comp. Ex. B2-2 | Hardening liquid 2 | Inkjet | 1.1 | Absent | B | B |
| Comp. Ex. B3-2 | Hardening liquid 2 | Inkjet | 0.1 | Present | C | C |
| Comp. Ex. B4-2 | Hardening liquid 2 | Inkjet | 18.7 | Absent | D | D |
| Comp. Ex. B5-2 | Hardening liquid 2 | Inkjet | 19.1 | Absent | D | D |

From the results of Table B3 and Table B4, Comparative Example B3-2 had cytotoxicity because of an excessively high phytic acid mixing amount of 51% by mass, and had a risk of expressing cytotoxicity when transplanted into a living body.

Comparative Example B1-2, Comparative Examples B2-2 to B4-2, and Comparative Example B5-2 had a HAp transformation rate of higher than 1%, and when transplanted into a living body, would have a trouble of transforming to hydroxyapatite (HAp) and remaining in the living body.

Preparation Example C1

Preparation of Layer Stack Formation Powder Material C1

Synthesis of α-Tricalcium Phosphate (α-TCP)

A 0.342 mol/dm$^3$ phosphoric acid aqueous solution was delivered at a speed of 6 mL/min into a 0.513 mol/dm$^3$ calcium hydroxide suspension liquid stirred with a commercially available paddle at 160 rpm, and their pH was stabilized to about 8.7 with ammonia. Then, the resultant was aged with an incubator of 37° C. for 72 hours, filtered, and then dried, to thereby obtain a powder product. Then, the powder product was burned under 800° C. conditions for 1 hour, and then subjected to ball mill pulverization with zirconia beads having a diameter of 3 mm. Here, ball mill pulverization was performed with BM-6 TYPE ROLLER BALL MILL manufactured by Glen Creston Ltd. When 30-minute pulverization was completed, the resultant was filtered through a 75 μm mesh, to thereby obtain minute particles. Then, the minute particles were burned at 1,400° C. for 5 hours, and then quenched, to thereby obtain α-tricalcium phosphate (α-TCP). The obtained α-tricalcium phosphate powder was classified with a pneumatic classifier (ELOBOW JET EJ-15 manufactured by Nittetsu Mining Co., Ltd.), and the resultant was used as a layer stack formation powder material C1.

The obtained α-TCP as the layer stack formation powder material C1 was measured in the same manner as in Preparation Example A2-1, and as a result, had a volume average particle diameter Dv of 4.7 μm, a granularity distribution Dv/Dn of 1.31, and an average circularity of 0.72.

A crystal phase of the calcium phosphate as the layer stack formation powder material C1 was identified in the same manner as in Preparation Example A2-1, and as a result, turned out to be α.

Preparation Example C2

Preparation of Layer Stack Formation Powder Material C2

Synthesis of Tricalcium Phosphate (β-TCP)

A 0.342 mol/dm$^3$ phosphoric acid aqueous solution was delivered at a speed of 6 mL/min into a 0.513 mol/dm$^3$ calcium hydroxide suspension liquid stirred with a commercially available paddle at 160 rpm, and their pH was stabilized to about 8.7 with ammonia. Then, the resultant was aged with an incubator of 37° C. for 72 hours, filtered, and then dried, to thereby obtain a powder product. Then, the powder product was burned under 800° C. conditions for 1 hour, and then subjected to ball mill pulverization with zirconia beads having a diameter of 3 mm. Here, ball mill pulverization was performed with BM-6 TYPE ROLLER BALL MILL manufactured by Glen Creston Ltd. When 30-minute pulverization was completed, the resultant was filtered through a 75 μm mesh, to thereby obtain minute particles. Then, the minute particles were burned at 1,100° C. for 5 hours, and then quenched, to thereby obtain β-tricalcium phosphate (β-TCP). The obtained β-tricalcium phosphate powder was classified with a pneumatic classifier (ELOBOW JET EJ-15 manufactured by Nittetsu Mining Co., Ltd.), and the resultant was used as a layer stack formation powder material C2.

The obtained β-TCP as the layer stack formation powder material C2 was measured in the same manner as in Preparation Example A2-1, and as a result, had a volume average particle diameter Dv of 4.5 μm, a granularity distribution Dv/Dn of 1.28, and an average circularity of 0.75.

A crystal phase of the calcium phosphate as the layer stack formation powder material C2 was identified in the same manner as in Preparation Example A2-1, and as a result, turned out to be 13.

Preparation Example C3

Preparation of Layer Stack Formation Powder Material C3

Synthesis of Octacalcium Phosphate (OCP)

A 0.342 mol/dm$^3$ phosphoric acid aqueous solution was delivered at a speed of 6 mL/min into a 0.455 mol/dm$^3$ calcium hydroxide suspension liquid stirred with a commercially available paddle at 160 rpm, and their pH was stabilized to about 8.7 with ammonia. Then, the resultant was aged with an incubator of 37° C. for 72 hours, filtered, and then dried, to thereby obtain a powder product. Then, the powder product was burned under 800° C. conditions for 1 hour, and then subjected to ball mill pulverization with zirconia beads having a diameter of 3 mm. Here, ball mill pulverization was performed with BM-6 TYPE ROLLER BALL MILL manufactured by Glen Creston Ltd. When 30-minute pulverization was completed, the resultant was filtered through a 75 pun mesh, to thereby obtain minute particles. Then, the minute particles were burned at 1,100° C. for 5 hours, and then quenched, to thereby obtain octacalcium phosphate (OCP). The obtained octacalcium phosphate powder was classified with a pneumatic classifier (ELOBOW JET EJ-15 manufactured by Nittetsu Mining Co., Ltd.), and the resultant was used as a layer stack formation powder material C3.

The obtained OCP as the layer stack formation powder material C3 was measured in the same manner as in Preparation Example A2-1, and as a result, had a volume average particle diameter Dv of 5.2 pun, a granularity distribution Dv/Dn of 1.34, and an average circularity of 0.76.

Preparation Example 4

Preparation of Hardening Agent-Containing Water C1

Water (59.5 parts by mass), a hardening agent, which was a citric acid (manufactured by Wako Pure Chemical Industries., Ltd.) (40 parts by mass), and a surfactant, which was TRITON X-100 (manufactured by Tokyo Chemical Industry Co., Ltd.) (0.5 parts by mass) were mixed, and dispersed with a homomixer for 5 minutes, to thereby prepare hardening agent-containing water C1.

Example C1

A layer stack object C1 was formed in the manner described below, using the obtained layer stack formation powder material C1 and hardening agent-containing water C1, and a shape printing pattern having a size of 70 mm in length and 12 mm in width.

(1) First, using such a publicly-known powder layer stack formation apparatus as shown in FIG. 1, the layer stack formation powder material C1 was delivered from the supply-side powder storage tank to the formation-side powder storage tank, to thereby form a thin layer of the layer stack formation powder material C1 having an average thickness of 100 µm over the support member.

(2) Next, using an inkjet printer (SG7100 manufactured by Ricoh Company, Ltd.), the hardening agent-containing water C1 was delivered (discharged) onto the surface of the formed thin layer of the layer stack formation powder material C1 from a nozzle, to harden the layer stack formation powder material C1, to thereby harden the calcium phosphate.

(3) Next, the operations (1) and (2) were repeated up to a predetermined total average thickness of 3 mm, and hardened thin layers of the layer stack formation powder material C1 were stacked up sequentially, to thereby form a layer stack object C1. The obtained layer stack object C1 was air-blown to remove any excess of the layer stack formation powder material, and as a result, did not have a shape collapse. The obtained layer stack object C1 was excellent in strength and dimensional precision.

Strength (hardness), and dimensional precision of the obtained layer stack object C1 were evaluated in the same manner as in Example A1-1. The results are shown in Table C1.

(4) The layer stack object C1 obtained in (3) was sintered in a sintering furnace under vacuum conditions at 1,300° C. The layer stack object C1 was a completely integrated calcium phosphate structure, and had no breakage or the like when slammed to a hard floor.

Example C2

A layer stack object C2 was formed in the same manner as in example C1, except that unlike in Example C1, the ball mill pulverization time was changed to 3 hours, to thereby change the volume average particle diameter Dv of α-TCP as the layer stack formation powder material C1 to 1.5 µm.

The obtained layer stack object C2 was evaluated in the same manner as in Example C1. The results are shown in Table C1.

Example C3

A layer stack object C3 was formed in the same manner as in Example C1, except that unlike in Example C1, the ball mill pulverization time was changed to 10 minutes, to thereby change the volume average particle diameter Dv of α-TCP as the layer stack formation powder material C1 to 7.0 µm.

The obtained layer stack object C3 was evaluated in the same manner as in Example C1. The results are shown in Table C1.

Example C4

A layer stack object C4 was formed in the same manner as in Example C1, except that unlike in Example C1, a rejection factor for removing minute particles and coarse particles in the classification was raised, to thereby change the granularity distribution Dv/Dn of α-TCP as the layer stack formation powder material C1 to 1.10.

The obtained layer stack object C4 was evaluated in the same manner as in Example C1. The results are shown in Table C1.

Example C5

A layer stack object C5 was formed in the same manner as in Example C1, except that unlike in Example C1, a rejection factor for removing minute particles and coarse particles in the classification was lowered, to thereby change the granularity distribution Dv/Dn of α-TCP as the layer stack formation powder material C1 to 1.40.

The obtained layer stack object C5 was evaluated in the same manner as in Example C1. The results are shown in Table C1.

Example C6

A layer stack object C6 was formed in the same manner as in Example C1, except that α-TCP as the layer stack formation powder material C1 used in Example C1 was changed to β-TCP the layer stack formation powder material C2.

The obtained layer stack object C6 was evaluated in the same manner as in Example C1. The results are shown in Table C1.

Example C7

A layer stack object C7 was formed in the same manner as in Example C1, except that α-TCP as the layer stack formation powder material C1 used in Example C1 was changed to OCP the layer stack formation powder material C3.

The obtained layer stack object C7 was evaluated in the same manner as in Example C1. The results are shown in Table C1.

Example C8

A layer stack object C8 was formed in the same manner as in Example C1, except that unlike in Example C1, the ball mill pulverization time was changed to 2 hours, to thereby change the average circularity of α-TCP as the layer stack formation powder material C1 to 0.70.

The obtained layer stack object C8 was evaluated in the same manner as in Example C1. The results are shown in Table C1.

Example C9

A layer stack object C9 was formed in the same manner as in Example C1, except that unlike in Example C1, the ball mill pulverization time was changed to 15 minutes, to thereby change the average circularity of α-TCP as the layer stack formation powder material C1 to 0.80.

The obtained layer stack object C9 was evaluated in the same manner as in Example C1. The results are shown in Table C1.

Example C10

A layer stack object C10 was formed as described below according to electron beam irradiation (EBM) instead of the ink jetting used in Example C1. Electron beam irradiation (EBM) was performed with a homebuilt electron beam irradiator.

(1) First, using such a publicly-known powder layer stack formation apparatus as shown in FIG. 1, the layer stack formation powder material C1 was delivered from the supply-side powder storage tank to the formation-side powder storage tank, to thereby form a thin layer of the layer stack formation powder material C1 having an average thickness of 100 µm over the support member.

(2) Next, an electron beam was emitted to the surface of the formed thin layer of the layer stack formation powder material C1, to sinter the layer stack formation powder material C1, to thereby sinter the calcium phosphate.

(3) Next, the operations (1) and (2) were repeated up to a predetermined total average thickness of 3 mm, and thin layers of the layer stack formation powder material C1 were stacked up sequentially, to thereby form a layer stack object C10.

The obtained layer stack object C10 was air-blown to remove any excess of the layer stack formation powder material C1, and as a result, did not have a shape collapse. The obtained layer stack object C10 was excellent in strength and dimensional precision.

The obtained layer stack object C10 was evaluated in the same manner as in Example C1. The results are shown in Table C1.

Example C11

A layer stack object C11 was formed as described below according to laser irradiation instead of the ink jetting used in Example C1. The laser used was a $CO_2$ laser (LP-400 manufactured by SUNX Co., Ltd.).

(1) First, using such a publicly-known powder layer stack formation apparatus as shown in FIG. 1, the layer stack formation powder material C1 was delivered from the supply-side powder storage tank to the formation-side powder storage tank, to thereby form a thin layer of the layer stack formation powder material C1 having an average thickness of 100 µm over the support member.

(2) The $CO_2$ laser was emitted to the surface of the formed thin layer of the layer stack formation powder material C1, to sinter the layer stack formation powder material C1, to thereby sinter the calcium phosphate.

(3) Next, the operations (1) and (2) were repeated up to a predetermined total average thickness of 3 mm, and thin layers of the layer stack formation powder material C1 were stacked up sequentially, to thereby form a layer stack object C11.

The obtained layer stack object C11 was air-blown to remove any excess of the layer stack formation powder material C1, and as a result, did not have a shape collapse. The obtained layer stack object C11 was excellent in strength and dimensional precision.

The obtained layer stack object C11 was evaluated in the same manner as in Example C1. The results are shown in Table C1.

Example C12

A layer stack object C12 was formed in the same manner as in Example C1, except that unlike in Example C1, the ball mill pulverization time was changed to 4 hours, to thereby change the average circularity of α-TCP as the layer stack formation powder material C1 to 0.71.

The obtained layer stack object C12 was evaluated in the same manner as in Example C1. The results are shown in Table C1.

Example C13

A layer stack object C13 was formed in the same manner as in Example C1, except that unlike in Example C1, the ball mill pulverization time was changed to 3 minutes, to thereby change the average circularity of α-TCP as the layer stack formation powder material C1 to 0.81.

The obtained layer stack object C13 was evaluated in the same manner as in Example C1. The results are shown in Table C1.

Example C14

A layer stack object C14 was formed in the same manner as in Example C1, except that unlike in Example C1, hardening agent-containing water C2, which was obtained by using a malic acid instead of the citric acid used in the hardening agent-containing water C1, was used. The obtained layer stack object C14 was evaluated in the same manner as in Example C1. The results are shown in Table C1.

Example C15

A layer stack object C15 was formed in the same manner as in Example C1, except that unlike in Example C1, hardening agent-containing water C3, which was obtained by using an edetic acid instead of the citric acid used in the hardening agent-containing water C1, was used. The obtained layer stack object C15 was evaluated in the same manner as in Example C1. The results are shown in Table C1.

Example C16

A layer stack object C16 was formed in the same manner as in Example C1, except that unlike in Example C1, hardening agent-containing water C4, which was obtained by using a succinic acid instead of the citric acid used in the hardening agent-containing water C1, was used. The obtained layer stack object C16 was evaluated in the same manner as in Example C1. The results are shown in Table C1.

Example C17

A layer stack object C17 was formed in the same manner as in Example C1, except that unlike in Example C1, hardening agent-containing water C5, which was obtained by using a phytic acid instead of the citric acid used in the hardening agent-containing water C1, was used. The obtained layer stack object C17 was evaluated in the same manner as in Example C1. The results are shown in Table C1.

Example C18

A layer stack object C18 was formed in the same manner as in Example C1, except that unlike in Example C1, hardening agent-containing water C6, which was obtained by using an alendronic acid instead of the citric acid used in the hardening agent-containing water C1, was used. The obtained layer stack object C18 was evaluated in the same manner as in Example C1. The results are shown in Table C1.

Example C19

A layer stack object C19 was formed in the same manner as in Example C1, except that unlike in Example C1, hardening agent-containing water C7, which was obtained by using an etidronic acid instead of the citric acid used in the hardening agent-containing water C1, was used. The obtained layer stack object C19 was evaluated in the same manner as in Example C1. The results are shown in Table C1.

TABLE C1

| | Kind of powder | Hardening agent-containing water | | Stacking method | Vol. ave. particle diameter: Dv (μm) | Ratio (Dv/Dn) | Average circularity | Evaluation of layer stack object | |
|---|---|---|---|---|---|---|---|---|---|
| | | Ink | Hardening agent | | | | | Strength | Dimensional precision |
| Ex. C1 | α-TCP | Ink 1 | Citric acid | Inkjet | 4.7 | 1.31 | 0.72 | B | B |
| Ex. C2 | α-TCP | Ink 1 | Citric acid | Inkjet | 1.5 | 1.14 | 0.79 | B | B |
| Ex. C3 | α-TCP | Ink 1 | Citric acid | Inkjet | 7.0 | 1.38 | 0.71 | B | B |
| Ex. C4 | α-TCP | Ink 1 | Citric acid | Inkjet | 4.1 | 1.10 | 0.78 | A | A |
| Ex. C5 | α-TCP | Ink 1 | Citric acid | Inkjet | 5.2 | 1.40 | 0.71 | B | B |
| Ex. C6 | β-TCP | Ink 1 | Citric acid | Inkjet | 4.5 | 1.28 | 0.75 | B | B |
| Ex. C7 | OCP | Ink 1 | Citric acid | Inkjet | 5.2 | 1.34 | 0.76 | B | B |
| Ex. C8 | α-TCP | Ink 1 | Citric acid | Inkjet | 6.9 | 1.33 | 0.70 | B | B |
| Ex. C9 | α-TCP | Ink 1 | Citric acid | Inkjet | 2.1 | 1.12 | 0.80 | B | B |
| Ex. C10 | α-TCP | — | — | Electron beam irradiation | 4.7 | 1.31 | 0.72 | A | A |
| Ex. C11 | α-TCP | — | — | $CO_2$ laser | 4.7 | 1.31 | 0.72 | A | A |
| Ex. C12 | α-TCP | Ink 1 | Citric acid | Inkjet | 4.5 | 1.33 | 0.71 | B | B |
| Ex. C13 | α-TCP | Ink 1 | Citric acid | Inkjet | 4.4 | 1.35 | 0.81 | C | C |
| Ex. C14 | α-TCP | Ink 2 | Malic acid | Inkjet | 4.7 | 1.31 | 0.72 | B | B |
| Ex. C15 | α-TCP | Ink 3 | Edetic acid | Inkjet | 4.7 | 1.31 | 0.72 | A | B |
| Ex. C16 | α-TCP | Ink 4 | Succinic acid | Inkjet | 4.7 | 1.31 | 0.72 | B | B |
| Ex. C17 | α-TCP | Ink 5 | Phytic acid | Inkjet | 4.7 | 1.31 | 0.72 | A | B |
| Ex. C18 | α-TCP | Ink 6 | Alendronic acid | Inkjet | 4.7 | 1.31 | 0.72 | B | B |
| Ex. C19 | α-TCP | Ink 7 | Etidronic acid | Inkjet | 4.7 | 1.31 | 0.72 | B | B |

Aspects of the present invention are, for example, as follows.

<1> A layer stack object formation method, including:
a layer forming step of forming a layer of a powder material containing calcium phosphate; and
a layer hardening step of delivering a hardening liquid to a predetermined region of the layer to thereby harden the region,
wherein the layer forming step and the layer hardening step are at least repeated, and
wherein 1) or 2) described below is satisfied,
1) the powder material satisfies A) or B) described below, and a hardened product obtained by hardening the powder material has a hydroxyapatite (HAp) transformation rate of 1% or lower,
A) an organic compound having phosphate group or carboxyl group is imparted over a surface of a powder of the calcium phosphate, and an imparting amount of the organic compound is 10,000 ppm or lower, and
B) the powder material further contains a powder made of an organic compound having phosphate group or carboxyl group, and a mixing amount of the organic compound relative to the powder of the calcium phosphate is 50% by mass or lower, and
2) the hardening liquid contains at least an organic compound having phosphate group or carboxyl group, an acid value of the organic compound is 0.45 gKOH/g or higher, and a content of the organic compound relative to a whole amount of the hardening liquid is 20% by mass or higher.
<2> The layer stack object formation method according to <1>, further including:
a sintering step of sintering a hardened layer stack object formed by repeating the layer forming step and the layer hardening step alternately.

<3> The layer stack object formation method according to <1> or <2>,
wherein the delivery of the hardening liquid is performed according to ink jetting.
<4> The layer stack object formation method according to any one of <1> to <3>,
wherein the organic compound has 2 or more phosphate groups per molecule, or 2 or more carboxyl groups per molecule.
<5> The layer stack object formation method according to any one of <1> to <4>,
wherein the organic compound having phosphate group has 2 or more phosphate groups per molecule.
<6> The layer stack object formation method according to any one of <1> to <5>,
wherein the organic compound having phosphate group is any of phytic acid and etidronic acid.
<7> The layer stack object formation method according to any one of <1> to <6>,
wherein the organic compound having carboxyl group has 3 or more carboxyl groups per molecule.
<8> The layer stack object formation method according to any one of <1> to <7>,
wherein the organic compound having carboxyl group is citric acid.
<9> The layer stack object formation method according to any one of <1> to <8>,
wherein the hardening liquid further contains inorganic particles.
<10> The layer stack object formation method according to <9>,
wherein the inorganic particles have a volume average particle diameter of 10 μm or less.
<11> The layer stack object formation method according to any one of <1> to <10>,
wherein the hardening liquid has a viscosity of from 5 mPa·s to 20 mPa·s at 20° C.
<12> The layer stack object formation method according to any one of <1> to <11>,
wherein the hardening liquid has a surface tension of 40 N/m or lower at 20° C.
<13> The layer stack object formation method according to any one of <1> to <12>,
wherein the imparting amount of the organic compound having phosphate group or carboxyl group in A) is from 1,000 ppm to 10,000 ppm.
<14> The layer stack object formation method according to any one of <1> to <13>,
wherein the calcium phosphate is at least one kind selected from the group consisting of β-tricalcium phosphate (β-TCP), α-tricalcium phosphate (α-TCP), and octacalcium phosphate (OCP).
<15> The layer stack object formation method according to any one of <1> to <14>,
wherein the powder material has a volume average particle diameter Dv of from 1.5 μm to 7.0 μm, and
wherein a ratio (Dv/Dn) of the volume average particle diameter Dv to a number average particle diameter Dn of the powder material is from 1.10 to 1.40.
<16> The layer stack object formation method according to any one of <1> to <15>,
wherein the powder material has an average circularity of from 0.70 to 0.80, where the average circularity is represented by the formula below, Average circularity=(a perimeter of a circle having a same area as a projected area of the powder material/a perimeter of a projected image of the powder material)×100.

<17> A powder layer stack formation hardening liquid, including at least:
an organic compound having phosphate group or carboxyl group,
wherein an acid value of the organic compound is 0.45 gKOH/g or higher, and a content of the organic compound relative to a whole amount of the powder layer stack formation hardening liquid is 20% by mass or higher.
<18> A layer stack formation powder material, including:
a calcium phosphate powder,
wherein the layer stack formation powder material satisfies A) or B) below, and
wherein a hardened product obtained by hardening the layer stack formation powder material has a hydroxyapatite (HAp) transformation rate of 1% or lower,
A) an organic compound having phosphate group or carboxyl group is imparted over a surface of the calcium phosphate powder, and an imparting amount of the organic compound is 10,000 ppm or lower, and
B) the layer stack formation powder material further contains a powder made of an organic compound having phosphate group or carboxyl group, and a mixing amount of the organic compound relative to the calcium phosphate powder is 50% by mass or lower.
<19> A layer stack formation material set, including:
a layer stack formation powder material containing calcium phosphate; and
a powder layer stack formation hardening liquid,
wherein the powder layer stack formation hardening liquid is the powder layer stack formation hardening liquid according to <17>, or
wherein the layer stack formation powder material is the layer stack formation powder material according to <18>.

This application claims priority to Japanese application No. 2014-052111, filed on Mar. 14, 2014 and incorporated herein by reference, Japanese application No. 2014-052119, filed on Mar. 14, 2014 and incorporated herein by reference, Japanese application No. 2014-052129, filed on Mar. 14, 2014 and incorporated herein by reference, Japanese application No. 2014-204782, filed on Oct. 3, 2014 and incorporated herein by reference, and Japanese application No. 2014-204804, filed on Oct. 3, 2014 and incorporated herein by reference.

What is claimed is:
1. A layer stack object formation method, comprising:
forming a layer of a powder material that comprises calcium phosphate; and
delivering a hardening liquid to a predetermined region of the layer to thereby harden the region,
wherein the formation and the hardening are repeated, and
wherein 1) or 2) described below is satisfied,
1) the powder material satisfies A) or B) described below, and a hardened product obtained by hardening the powder material has a hydroxyapatite (HAp) transformation rate of 1% or lower,
A) an organic compound having phosphate group or carboxyl group is imparted over a surface of a powder of the calcium phosphate, and an imparting amount of the organic compound is 10,000 ppm or lower, and
B) the powder material further comprises a powder made of an organic compound having phosphate group or carboxyl group, and a mixing amount of the organic compound relative to a powder of the calcium phosphate is 50% by mass or lower, and
2) the hardening liquid comprises an organic compound having phosphate group or carboxyl group, an acid value of the organic compound is 0.45 gKOH/g or higher, and a content of the organic compound relative to a whole amount of the hardening liquid is 20% by mass or higher.

2. The layer stack object formation method according to claim 1, further comprising:
sintering a hardened layer stack object formed by repeating the formation and the hardening alternately.

3. The layer stack object formation method according to claim 1,
wherein the delivery of the hardening liquid is performed according to ink jetting.

4. The layer stack object formation method according to claim 1,
wherein the organic compound has 2 or more phosphate groups per molecule, or 2 or more carboxyl groups per molecule.

5. The layer stack object formation method according to claim 1,
wherein the organic compound having phosphate group has 2 or more phosphate groups per molecule.

6. The layer stack object formation method according to claim 1,
wherein the organic compound having phosphate group is any of phytic acid and etidronic acid.

7. The layer stack object formation method according to claim 1,
wherein the organic compound having carboxyl group has 3 or more carboxyl groups per molecule.

8. The layer stack object formation method according to claim 1,
wherein the organic compound having carboxyl group is citric acid.

9. The layer stack object formation method according to claim 1,
wherein the hardening liquid further comprises inorganic particles.

10. The layer stack object formation method according to claim 9,
wherein the inorganic particles have a volume average particle diameter of 10 µm or less.

11. The layer stack object formation method according to claim 1,
wherein the hardening liquid has a viscosity of from 5 mPa·s to 20 mPa·s at 20° C.

12. The layer stack object formation method according to claim 1,
wherein the hardening liquid has a surface tension of 40 N/m or lower at 20° C.

13. The layer stack object formation method according to claim 1,
wherein the imparting amount of the organic compound having phosphate group or carboxyl group in A) is from 1,000 ppm to 10,000 ppm.

14. The layer stack object formation method according to claim 1,
wherein the calcium phosphate is at least one kind selected from the group consisting of β-tricalcium phosphate (β-TCP), α-tricalcium phosphate (α-TCP), and octacalcium phosphate (OCP).

15. The layer stack object formation method according to claim 1,
wherein the powder material has a volume average particle diameter Dv of from 1.5 µm to 7.0 µm, and
wherein a ratio (Dv/Dn) of the volume average particle diameter Dv to a number average particle diameter Dn of the powder material is from 1.10 to 1.40.

16. The layer stack object formation method according to claim 1,
wherein the powder material has an average circularity of from 0.70 to 0.80, where the average circularity is represented by the formula below, Average circularity=(a perimeter of a circle having a same area as a projected area of the powder material/a perimeter of a projected image of the powder material)×100.

17. A powder layer stack formation hardening liquid, comprising:
an organic compound having phosphate group or carboxyl group,
wherein an acid value of the organic compound is 0.45 gKOH/g or higher, and a content of the organic compound relative to a whole amount of the powder layer stack formation hardening liquid is 20% by mass or higher.

18. A layer stack formation powder material, comprising:
a calcium phosphate powder,
wherein the layer stack formation powder material satisfies A) or B) below, and
wherein a hardened product obtained by hardening the layer stack formation powder material has a hydroxyapatite (HAp) transformation rate of 1% or lower,
A) an organic compound having phosphate group or carboxyl group is imparted over a surface of the calcium phosphate powder, and an imparting amount of the organic compound is 10,000 ppm or lower, and
B) the layer stack formation powder material further comprises a powder made of an organic compound having phosphate group or carboxyl group, and a mixing amount of the organic compound relative to the calcium phosphate powder is 50% by mass or lower.

19. A layer stack formation material set, comprising:
a layer stack formation powder material that comprises calcium phosphate; and
a powder layer stack formation hardening liquid,
wherein the powder layer stack formation hardening liquid is the powder layer stack formation hardening liquid according to claim 17, or
wherein the layer stack formation powder material is the layer stack formation powder material according to claim 18.

* * * * *